United States Patent
Armstrong et al.

(10) Patent No.: US 6,608,716 B1
(45) Date of Patent: Aug. 19, 2003

(54) OPTICAL ENHANCEMENT WITH NANOPARTICLES AND MICROCAVITIES

(75) Inventors: Robert L. Armstrong, Las Cruces, NM (US); Vladimir M. Shalaev, Las Cruces, NM (US); Thomas M. Shay, Albuquerque, NM (US); Won-Tae Kim, Las Cruces, NM (US); Z. Charles Ying, Las Cruces, NM (US); Vladimir P. Drachev, Las Cruces, NM (US); Vladimir P. Safonov, Novosibirsk (RU)

(73) Assignee: New Mexico State University Technology Transfer Corporation, Las Cruces, NM (US)

( * ) Notice: Subject to any disclaimer, the term of this patent is extended or adjusted under 35 U.S.C. 154(b) by 0 days.

(21) Appl. No.: 09/572,721

(22) Filed: May 16, 2000

Related U.S. Application Data

(60) Provisional application No. 60/134,564, filed on May 17, 1999, and provisional application No. 60/190,863, filed on Mar. 20, 2000.

(51) Int. Cl.⁷ ................................. H01S 3/00
(52) U.S. Cl. ....................................... 359/342
(58) Field of Search .......................... 359/342; 356/301

(56) References Cited

U.S. PATENT DOCUMENTS

| | | |
|---|---|---|
| 4,781,458 A | 11/1988 | Angel et al. |
| 4,828,758 A | 5/1989 | Gillberg-LaForce et al. |
| 4,903,272 A | 2/1990 | Simic-Glavaski |
| 4,913,845 A | 4/1990 | Gillberg-LaForce et al. |
| 5,234,758 A | 8/1993 | Olsen et al. |
| 5,327,211 A | 7/1994 | Carron et al. |
| 5,405,710 A | 4/1995 | Dodabalapur et al. |
| 5,405,906 A | 4/1995 | Olsen et al. |
| 5,449,918 A | 9/1995 | Krull et al. |
| 5,468,366 A | 11/1995 | Wegner et al. |
| 5,469,018 A | 11/1995 | Jacobsen et al. |
| 5,478,658 A | 12/1995 | Dodabalapur et al. |
| 5,527,712 A | 6/1996 | Sheehy |
| 5,609,907 A | 3/1997 | Natan |
| 5,616,986 A | 4/1997 | Jacobsen et al. |
| 5,674,636 A | 10/1997 | Dodabalapur et al. |
| 5,777,776 A | 7/1998 | Hiraga et al. |
| 5,837,552 A | 11/1998 | Cotton et al. |
| 5,853,464 A | 12/1998 | Macpherson et al. |
| 5,866,433 A | 2/1999 | Schalkhammer et al. |
| 5,939,021 A | 8/1999 | Hansen et al. |
| 5,952,655 A | 9/1999 | Bhargava |
| 5,990,479 A | 11/1999 | Weiss et al. |
| 6,025,202 A | 2/2000 | Natan |
| 6,149,868 A | 11/2000 | Natan et al. |
| 6,214,560 B1 | 4/2001 | Yguerabide et al. |
| 6,242,264 B1 | 6/2001 | Natan et al. |
| 6,417,340 B1 | 7/2002 | Mirkin et al. |

OTHER PUBLICATIONS

Andrews et al., "Integrated optics waveguide spectroscopy of self–organizing polymers and fractal composites", Proceedings of the SPIE, vol. 2042, pp. 366–375, 1994.*

Silman, O., et al., "Surface–Enhanced Raman Scattering by Citrate on Coloidal Silver," *J of Phys. Chem.*, vol. 87, No. 6, pp 1014–1023.

(List continued on next page.)

*Primary Examiner*—F. L. Evans
(74) *Attorney, Agent, or Firm*—Jeffrey D. Myers; Deborah A. Peacock; Andrea L. Mays

(57) ABSTRACT

A method and apparatus for enhanced optical emissions, the apparatus comprising a light source, a microcavity, and a medium comprising nanoparticles, located within or near the microcavity. The nanoparticles are either non-aggregated or are aggregated in the form of fractals. The nanoparticles and microcavity exhibit enhanced linear and non-linear optical emission. The light emitting apparatus can be used for wavelength translation, amplification, optical parametric oscillation, light detection and ranging, increased sensitivity, high density optical data storage, and near-field optical spectroscopy.

46 Claims, 12 Drawing Sheets

OTHER PUBLICATIONS

Biswas, A., et al., "Time–Resolved Spectroscopy of Laser Emission from Dye–doped Droplets," *Optics Letters*, vol. 14, No. 4, pp 214–216 (Feb. 15, 1989).

Boyd, R.W., et al., "Nonlinear Optical Properties of Nanocomposite Materials," *Pure Appl. Opt.*, vol. 5, pp 505–512 (1996).

Chang, R.K., et al., Textbook: "Optical Processes in Microcavities," *World Sciencific*, Singapore–New Jersey–London–Hong Kong (1996) Table of Contents for reference.

Chang. R.K., et al. Textbook: "Surface Enhanced Raman Scattering," *Plenum Press*, New York–London (1982) Table of Contents for reference.

Chinn, S.R., "Analysis of Counter–Pumped Small–Signal Fiber Raman Amplifiers," *Electronics Letters*, vol. 33, No. 7, pp 607–608 (Mar. 27, 1997).

Kerker, M., et al., "Surface Enhanced Raman Scattering (SERS) of Citrate Ion Adsorbed on a Colloidal Silver," *Applied Optics*, vol. 19, No. 19, pp 3253–3255 (Oct. 1, 1980).

Kneipp, K., et al., "Single Molecule Detection Using Surface–Enhanced Raman Scattering (SERS)",*Physical Review Letters*, vol. 78, No. 9, pp 1667–1970, (Mar. 3, 1997).

Lee, P.C., et al., "Adsorption and Surface–Enhanced Raman of Dyes on Silver and Gold Sols," *J. Phys. Chem.*, vol. 86, pp 3391–3395 (1982).

Lin,H.B., et al., "cw Nonlinear Optics in Droplet Microcavities Displaying Enhanced Gain," *Phys. Rev. Letters*, vol. 73, No. 18, pp 2440–2443 Oct. 31, 1994.

Markel, V.A., et al., "Small–Particle Composites. I. Linear Optical Properties," *Phys. Review B*, vol. 53, No. 5, pp 2425–2436 (Feb. 1, 1996).

Markel, V.A., "Theory and Numerical Simulation of Optical Properties of Fractal Clusters," *Phys. Rev. B*, vol. 43, No. 10, pp 8183–8195 (Apr. 1, 1991).

Moskovits, M., "Surface–Enhanced Spectroscopy," *Rev. Mod. Phys.*, vol. 57, No. 3, Part I, pp 783–826 (Jul. 1985).

Nie, S., et al., "Probing Single Molecules and single Nanoparticles by Surface–Enhanced Raman Scattering," *Science*, vol. 275, pp 1102–1106 (Feb. 21, 1997).

Owen, J.F., et al., "Enhancement of Fluorescense Induced by Microstructure Resonances of a Dielectric Fiber," *Phys. Rev. Letters*, vol. 47, No. 15, pp 1975–1078 (Oct. 12, 1981).

Prasler, M.A., et al., Textbook: "Near–Field Optics: Theory, Instrumentation, and Applications," *Wiley–Interscience Publication*, John Wiley & Sons, Inc., New York (1996) Table of Contents for reference.

Rautian, S.G., et al., "Surface–Enhanced Parametric Scattering of Light by Silver clusters," *JETP Lett.*, vol. 47, No. 4, pp 243–246 (Feb. 25, 1988).

Ritchie, G., et al., "Luminescence of Dye Molecules Adsorbed at a Ag Surface," *Phys. Rrev. B*, vol. 24, No. 8, pp 4843–4846 (Oct. 15, 1981).

Safonov, V.P., et al., spectral Dependence of Selective Photomodification in Fractal Aggregates of Colloidal Particles, *Phys. Rev. Lett.*, vol. 80, No. 5, pp 1102–1105 (Feb. 2, 1998).

Shalaev, V.M., et al., "Optical Properties of Fractal Clusters (susceptibility, Surfae Enhanced Raman Scattering by Impurities," *Sov. Phys. JETP*, vol. 65, No. 2, pp 287–294 (Feb. 1987).

Shalaev, V.M., et al., "Electromagnetic Properties of Small––Particle Composites," *Phys. Reports*, vol. 272, pp 61–137 (1996).

Shalaev, V.M., "Nonlinear Optical Phenomena in Nanostructured Fractal Materials," *J. Nonlinear Op. Phys. & Mat.,*, vol. 7, No. 1, pp 131–152 (1998).

Shalaev., V.M., et al., "Small Particle Composites. II Nonlinear Optical Properties," *Phys. Rev. B*, vol. 53, No. 5, pp 2437–2449 (Feb. 1, 1996).

Stockman. M.I., "chaos and spatial Correlations for Dipolar Eigenproblems," *Phys. Rev. Lett.*, vol. 79, No. 23, pp 4562–4565 (Dec. 8, 1997).

Tzeng, H.M., et al., "Laser emission from Individual Droplets at Wavelengths Corresponding to Morphology–Dependent Resonances," *Optics Lett.*, vol. 9, No. 11, pp 499–501 (Nov. 1984).

Yariv, A., Textbook: "Quantum Electronics", Third Edition, *John Wiley & Sons*, New York, pp 466—467 and Table of Contents for reference.

Xu, X–H, et al., "Direct Measurement of single–Molecule Diffusion and Photodecomposition in Free Solution," *Science,*, vol. 275, pp 1106–1109 (Feb. 21, 1997).

Shibata, S., et al., "Preparation of Silica Microspheres Containing AG Nanoparticles," *Journal of Sol–Gel Sci and Tech*, Kluwer Academic Publishers, Dordrecht, NL, vol. 11, No. 3 (Aug. 1, 1998) pp. 279–287.

Shalaev, V.M. et al., "Nonlinear Optical Phenomena in Nanostructured Fractal Materials," *J. of Nonlinear Optical Physics and Materials*, Mar. 1998, World Scientific, vol. 7, No. 1 (Mar. 1998) pp. 131–152.

Wang, H.Z. et al., "Low–Threshold Lasing of A, Rhodamine Dye Solution Embedded with Nanoparticle Fractal Aggregates," *Optics Letters*, Optical Society of America, Washington US, vol. 23, No. 10 (May 15, 1998) pp. 777–779.

Kurokawa Y., et al., "Surface–Enhanced Raman Spectroscopic Detetion of Carbonate, Sulfate, and Nucleic Acid Bases Using Polyvinyl Alcohol Film Doped with Silver Fine Particles," *Analytical Biochemistry*, vol. 209, No. 2 (1993) pp. 247–250.

Kim, W., et al., "Fractals in Microcavities: Giant Coupled, Multiplicative Enhancement of Optical Responses," *physical Review Letters*, Jun. 14, 1999, PAS, USA, vol. 82, No. 24, pp. 4811–4814.

Shubin, V.A., et al., "Surface–Plasmon–Enhanced Radiation Effects in Confined Photonic Systems" *Journal of Lightwave Technology, IEEE*, New York US, vol. 17, No. 11 (Nov. 11) pp. 2183–3190.

Moskovits, M., "Surface–Enhanced Spectroscopy" *Reviews of Modern Physics, American Physical Soc.*, vol. 57, No. 3, Part 1 (Jul. 1985) pp. 783–826.

Chang, R.K., (Campillo A.J, eds) "Optical Processes in Microcavities" (1996) World Scientific, Singapore pp. 257–283.

Purcell, E.M., "Spontaneous Emission Probabilities at Radio Frequencies", Physical Review, vol. 69, No. 11–12 (Jun. 1–5, 1946), page 681 and whole document.

Marvel, V.A. et al., "Small Particle Composites –Linear Optical Properties, " Phys. Rev B. condensed matter, vol. 53, No. 5, pp. 2425–2436 (Feb. 1, 1996).

Shalaev, V.M. et al., "Small Partcle Composites –Nonlinear Optical Properties," Physical Review B condensed matter, vol. 53, No. 5, pp.. 2437–2449.

* cited by examiner

OPTICAL ENHANCEMENT WITH NANOPARTICLES AND MICROCAVITIES

CROSS-REFERENCE TO RELATED APPLICATIONS

This application claims the benefit of U.S. Provisional Application(s) No(s).:

Ser. No. 60/134,564 May 17, 1999. and

Ser. No. 60/190,863 Mar. 20, 2000

GOVERNMENT RIGHTS

The U.S. Government has a paid-up license in this invention and-the right in limited circumstances to require the patent owner to license others on reasonable terms as provided for by the terms of National Science Foundation Contract Nos. DMR 9623663 and DMR 9810183, by ARO under grant DAAG55-98-1-0425 awarded by the U.S. Army, and under New Mexico Universities Collaborative Research (NUCOR) Program grant numbers 9882 and 9964.

BACKGROUND OF THE INVENTION

1. Field of the Invention (Technical Field)

The present invention relates to enhancing linear and nonlinear optical emission using nanoparticles, wherein the nanoparticles are either non-aggregated or aggregated, and microcavities. The aggregrated nanoparticles comprise fractals. Microcavities are used in combination with nanoparticles for greatly enhanced optical emission.

2. Background Art

Recently, fractal aggregates of gold, silver, and other noble metals have received attention in the field of linear and nonlinear optical research. Fractals comprise aggregates of particles in colloidal solutions, sols and gels, and soot and smoke. Also, most macromolecules exist in the form of fractals. A fractal aggregate is a system of interacting particles, with special scale-invariant geometry. Scale-invariance in particle aggregates manifests itself in spacial scales larger than the sizes of particles forming the cluster and smaller than the size of the whole cluster; therefore, to track the fractal geometry in a single aggregate it must be relatively large. However, an ensemble of small aggregates of particles, with the number of particles on the order of only ten or more, can also manifest the fractal geometry statistically, on average, despite the fact that single clusters do not manifest the fractal geometry when considered individually. Thus, the term fractals comprises an ensemble of large aggregates (the ensemble can be small and consist of few, or even one, cluster), or a large ensemble of small aggregates of particles, which statistically show the fractal (scale-invariant) geometry with some interval of sizes.

Enhanced optical response in metal nanocomposites characterized by fractal geometry and thin metallic films containing nanoscale surface features has been intensively studied. R. K. Chang and T. E. Furtak, Ed., *Surface Enhanced Raman Scattering* (Plenum Pres, NY, 1982); M Moskovits, Rev. Mod. Phys. 57, 783 (1985); R. W. Boyd, et al., Pure Appl. Opt. 5, 505 (1996); V. M. Shalaev and M. I. Stockman, Sov. Phys. JETP 65, 287 (1987); V. A. Markel, et al., Phys. Rev. B 43, 8183 (1991); V. M. Shalaev, Phys. Reports 272, 61 (1996); V. A. Markel, et al., Phys. Rev. B 53, 2425 (1996); V. M. Shalaev, et al., Phys. Rev. B 53, 2437 (1996); M. I. Stockman, Phys. Rev. Lett. 79, 4562 (1997); S. G. Rautian, et al., JETP Lett. 47, 243 (1988); V. P. Safonov et al., Phys. Rev. Lett 80, 1102 (1998); V. M. Shalaev et al., J. Nonlinear Optical Physics and Materials 7, 131 (1998).

Enhancement in the optical response is associated with the excitation of surface plasmons, collective electromagnetic modes whose characteristics are strongly dependent on the geometrical structure of the metallic component of the medium. Collective optical excitations, such as surface plasmons, are often spatially localized in fractals. This localization leads to the presence of nanometer-scale spatial regions of high local electric fields, "hot spots", and accordingly, to significant enhancement for a variety of optical processes, such as Raman scattering, four-wave mixing, and nonlinear absorption and refraction. In some cases, the local enhancement at a hot spot can be $10^9$ greater than the average enhancement resulting from the fractal itself, averaged over the entire surface of the fractal.

Fractals also have another important property—they are subject to surface enhanced Raman scattering (SERS) by adsorbed molecules. Suitable substrates known to exhibit SERS include colloidal metal particles, vacuum deposited films, single crystals, and matrix isolated metal clusters. O. Silman, et al., J. Phys. Chem. 87, 1014–23 (1983). Also, adsorption of dye molecules, e.g., Rhodamine 6G (R6G), on colloidal Ag or Au is known. P. C. Lee and D. Melsel, J. Phys. Chem. 86, 3391–95 (1982). Once adsorbed onto the colloidal particle, the dye may exhibit strong surface enhanced Raman scattering.

Fractal aggregates of metal nano-sized particles can provide dramatic enhancement for various linear and nonlinear optical responses, including Raman Scattering (RS) and Hyper-Raman Scattering (HRS). This occurs because of localization of optical plasmon excitations within small parts of a fractal aggregate, hot spots, smaller than the size of the fractal and often smaller than the wavelength. When sufficiently concentrated, the large electromagnetic fields in the hot spots can result in very large enhancement of optical responses. The small areas, where the fractal optical excitations are localized, have very different local structures and, therefore, they are characterized by different resonant frequencies. Because of the large variety in local geometries of fractal hot spots, the normal modes of a fractal aggregate cover a huge spectral range, from the near ultra-violet to the far-infrared, leading to giant enhancement of optical responses within this large spectral range. Furthermore, since the dielectric constant of metal is negative and increases in magnitude toward the longer wavelengths, the enhancement for optical processes becomes progressively larger toward infrared (IR) wavelengths.

The various nano-scale areas, where the resonant fractal excitations are localized, can be thought of as a set of different optical "nano-resonators", each having different resonance frequencies resonating in the visible and IR spectral ranges. These fractal nano-resonators have large resonance quality-factors (Q), representing the local-field enhancement, that increase from the visible to the IR region of the spectrum.

Large enhancement for SERS can also be obtained in compact structures, such as nano-sized spheroids or small chain-like aggregates of particles. However, a compact structure of a given geometry has very few normal modes, for example, one, in a sphere, and three, in a spheroid, and thus provide enhancement at only a few selected frequencies. In contrast, in random fractals, there are always such configurations of particles (nano-resonators) that resonate at any given wavelength. Thus, the inherent properties of random fractals provide localization of optical excitations which become sensitive to the local structures. In addition, the fractals exist as a large variety of resonating local structures, which leads to a very broad enhancement band from the near ultra-violet to the far-infrared region of the spectrum.

An alternative approach for achieving large enhancement of the optical response involves the excitation of morphology-dependent resonances (MDRs) in dielectric microcavities. R. K. Chang and A. J. Campillo, Ed., *Optical Processes in Microcavities,* World Scientific, Singapore-New Jersey-London-Hong Kong (1996). These resonances, which may have very high quality factors, Q on the order of $10^5$ to $10^9$, result from confinement of the radiation within the microcavity by total internal reflection. Light emitted or scattered in the microcavity may couple to the high-Q MDRs lying within its spectral bandwidth, leading to enhancement of both spontaneous and stimulated optical emissions. For example, enhanced fluorescence emission from a dye-doped cylindrical or spherical microcavity occurs when either the laser pump or the fluorescence, or both, couple to microcavity MDRs. J. F. Owen, Phys. Rev. Lett. 47, 1075 (1981). Moreover, the increased feedback produced by MDRs is sufficient to obtain laser emission from a dye-doped microdroplet under both a continuous wave (CW) and pulsed laser excitation. H. M. Tzeng, et al., Opt. Lett. 9, 499 (1984); A. Biswas, et al., Opt. Lett. 14, 214 (1988). The existence of high-Q microcavity modes is also responsible for numerous stimulated nonlinear effects including stimulated Raman and Rayleigh-wing scattering and four-wave parametric oscillation under moderate intensity CW excitation. M. B. Lin and A. J. Campillo, Phys. Rev. Lett. 73, 2440 (1994).

Optical microcavities are resonators that have at least one dimension, on the order of a single or at most a small integral number of optical wavelengths. See Dodabalapur, et al., U.S. Pat. No. 5,405,710, entitled "Article Comprising Microcavity Light Sources." The specific geometry of the microcavity and the boundary conditions on the interface of the dielectric-to-air impose selective normal modes on the optical microcavity. Typical microcavities have diameters of 100 microns or less. Such microcavities have shown technological promise for constructing novel light emitting devices. Possible applications of microcavities devices include flat panel displays, optical interconnects, optical fiber communications, and light emitting diode (LED) printing. For example, in a display application, a device may consist of three microcavities, each microcavity emitting in the blue, green, and red regions of the visible spectrum. Further, resonant microcavities have the advantage of emitting light in a highly directional manner as a result of their inherent geometry.

As described briefly above fractal aggregates and resonating microcavities are known to cause large enhancements of optical emissions. The present invention uses the properties of nanoparticles, fractals, and microcavities to enhance optical emissions for a variety of apparatuses and methods. The present invention further combines the properties of these optical enhancement processes by placing nanoparticles and/or fractal aggregates within a high-Q microcavity. Overall, the observed optical enhancement of the invention is multiplicative rather than additive of the two processes. Results demonstrate the unique potential of such devices in the development of ultra-low threshold microlasers, nonlinear-optical devices for photonics, as well as new opportunities of micro-analysis, including spectroscopy of single molecules.

SUMMARY OF THE INVENTION
(DISCLOSURE OF THE INVENTION)

The present invention is a light emitting apparatus that is comprised of at least one light source, such as a laser, and a medium that is made up of nanoparticles. These nanoparticles can either be non-aggregated nanoparticles and/or aggregated nanoparticles, wherein the aggregated nanoparticles comprise fractals. Preferably, each fractal comprises at least ten aggregated nanoparticles, and furthermore each fractal comprises a dimension less than that of the embedding space. The apparatus can further comprise a microcavity. The medium is then located in the vicinity of the microcavity in order to enhance the optical emission. To be in the vicinity of the microcavity, the medium is located within a light wavelength of the surface of the microcavity or within the boundaries of the microcavity. The microcavity can be either solid or hollow. When the microcavity is solid, the medium can either be located on a surface of the microcavity or embedded within the microcavity. When the microcavity is hollow, the medium can either be located within the hollow microcavity or on a surface of the hollow microcavity. The microcavity can be either cylindrical, spherical, spheroidal, polyhedral, or an optical wave guide microcavity. The exterior dimension of the microcavity is preferably at least twice that of the optical wavelength of interest.

The medium can further be contained within a liquid suspension, gel matrix, or solid matrix. The medium itself can be of metal, semi-metal, and/or a semiconductor. Metals that can be used for the medium can be either silver, gold, platinum, copper, aluminum, or magnesium. The semi-metal can be graphite. Any of Group IV, Group III-V, or Group II-VI semiconductors can be used.

Preferably the average diameter of each individual nanoparticle is less than that of the optical wavelength of interest. The light source, such as a pump laser, for the present invention preferably emits light of wavelengths between approximately 200 and 100,000 nanometers, more preferably between approximately 300 and 2,000 nanometers. The light source also emits light, having between approximately 1 nanowatt and 100 watts of power.

Optionally, at least one optically active organic and/or inorganic molecule is adsorbed on a surface of the nanoparticles. For example, laser dye or sodium citrate molecules can be adsorbed on a surface of the nanoparticles. The laser dye can be a xanthene, coumarin, pyrromethene, styryl, cyanine, carbon-bridged, naphthofluorescein-type, acridone, quinalone derivative, p-terphenyl, p-quaterphenyl, or a 9-aminoacridine hydrochloride dye. In the alternative, at least one optically active organic and/or inorganic molecule is located within the light wavelength of the surface of the nanoparticles. Again, such a molecule can be either a laser dye or sodium citrate molecules.

The present invention is also a method of enhancing the optical emission of a material and comprises the steps of doping a medium, wherein the medium comprises a plurality of nanoparticles, either non-aggregated nanoparticles and/or aggregated nanoparticles, and exciting the doped medium with at least one light source. The aggregated nanoparticles are fractals. The medium can be doped with at least one material from the materials including a single molecule, a plurality of molecules, a nanocrystal, a solid matrix, DNA, DNA fragments, amino acids, antigen, antibodies, bacteria, bacterial spores, and viruses. The method can further include the step of locating the doped medium in the vicinity of a microcavity. Locating can comprise locating the medium on a surface of a solid microcavity or embedding the medium within a solid microcavity. Alternatively, the locating step can comprise locating the medium within a hollow microcavity, or alternatively locating the medium on a surface of a hollow microcavity.

When exciting the medium, the exciting step can comprise exciting the doped medium to result in at least one type of optical process, such as photoluminescence, Raman scattering, hyper-Raman scattering, Broullion scattering, harmonic generation, sum frequency generation, difference frequency generation, optical parametric processes, multi-photon absorption, optical Kerr effect, four-wave mixing, and phase conjugation. Optionally, the method further comprises containing the medium within a substance such as a liquid suspension, a gel matrix, or a solid matrix. The doped medium can comprise metal, semi-metal, and/or a semiconductor. Examples of metals include silver, gold, platinum, copper, aluminum, and magnesium. The semi-metal can comprise graphite, and the semiconductor can be any of either Group IV, Group III-V, or Group II-VI semiconductors.

The exciting step preferably comprises emitting light of wavelengths between approximately 200 and 100,000 nanometers, more preferably between 300 and 2,000 nanometers, and wherein the light emitted has between anywhere from approximately 1 nanowatt to 100 watts of power.

The doping step can further comprise doping with at least one optically active organic and/or inorganic molecule located within the light wavelengths of the surface of the medium. These molecules can be, for example, laser dye or sodium citrate molecules.

Furthermore, the present invention provides a wavelength translation apparatus, wherein the apparatus comprises at least one light source and a medium made up of a plurality of nanoparticles, wherein the nanoparticles are either non-aggregated nanoparticles and/or fractals comprised of aggregated nanoparticles. The wavelength translation apparatus can further include a microcavity and a medium, wherein the medium is located in the vicinity of the microcavity to enhance optical emission. The methodology for wavelength translation comprises the steps of providing the medium having a plurality of nanoparticles, be it either non-aggregated and/or aggregated nanoparticles, and exciting the medium with a light source, such as a laser. The method can further include the step of locating the medium in the vicinity of a microcavity to amplify optical emission. Locating the medium in the vicinity of a microcavity to amplify optical emission further comprises amplifying the optical emission via at least one of the following processes: stimulated emission of photons, stimulated Raman scattering, stimulated hyper-Raman scattering, stimulated Broullion scattering, optical parametric amplification, multi-photon emission, four-wave mixing, and phase conjugation.

The present invention further provides an amplifying apparatus having a gain greater than 1.2 and consists of at least one light source, a microcavity, and a medium made up of a plurality of nanoparticles, being either non-aggregated and/or aggregated nanoparticles, and wherein the medium is located in the vicinity of the microcavity to enhance optical emission. The method of amplification comprises providing the medium and locating it within the vicinity of a microcavity to amplify the optical emission, as well as exciting the medium with at least one light source, such as a laser.

The present invention further provides for an optical parametric oscillator comprising at least one light source, a cavity, and a medium wherein the medium comprises a plurality of nanoparticles. The nanoparticles can be non-aggregated nanoparticles and/or aggregated nanoparticles. The aggregated nanoparticles comprise fractals. The medium is located in the vicinity of the cavity to enhance optical emission. Preferably the cavity comprises a microcavity.

The present invention further provides for a light detection and ranging system comprising a transmitter light source; a receiver to receive light produced from the interaction of the transmitter light with constituents; and a medium. The medium comprises a plurality of nanoparticles and the nanoparticles can be non-aggregated and/or aggregated nanoparticles. The light detection and ranging system further comprises a microcavity to receive light from the receiver, wherein the medium is located in the vicinity of the microcavity to amplify the received light.

The present invention still further provides a method of optical data storage and comprises the steps of providing a medium, wherein the medium comprises a plurality of nanoparticles. The nanoparticles can be non-aggregated nanoparticles and/or aggregated nanoparticles. The method further includes the steps of irradiating the medium with polychromatic light and generating hot spots in the medium due to intensity differences of different wavelengths, and spectral hole burning the medium due to photomodification, thereby creating high density storage capabilities. The method for optical data storage can further comprise the step of locating the medium in the vicinity of a microcavity to amplify optical emission.

The present invention still further provides for near-field optical spectroscopy. This method provides for spatial resolution on the order of 1 nanometer. One method for detecting materials with near-field optics comprises locating the material within a distance shorter than the light wavelength from a tapered end of an optical fiber and detecting the light emitted from the material through the optical fiber. A second method for detecting a material with near-field optics comprises locating a tapered end of an optical fiber within a distance shorter than the light wavelength from the material in order to illuminate the material. A third method of detecting a material using near-field optics comprises locating a sharp tip of a vibrating metal wire within a distance shorter than the light wavelength from the material, and detecting the light emitted from the material with a lock-in method. In all of these methodologies, the material to be detected is located within a distance shorter than the light wavelength from either a tapered end of an optical fiber or a sharp tip of a vibrating metal wire.

Near-field optical spectroscopy is a near-field optical spectroscopic method for detecting chemical compounds and biological materials through their spectroscopic signatures. The present invention is further of near-field optical spectroscopy by increasing the ability to detect any of the following materials: a single molecule, a plurality of molecules, a nanocrystal, DNA, DNA fragments, amino acids, antigen, antibodies, bacteria, bacterial spores, or viruses. The method further comprises obtaining spectroscopic signatures such as electronic, vibrational or rotational spectroscopic signatures. The method can further include an optical process such as photoluminescence, Raman scattering, hyper-Raman scattering, Broullion scattering, harmonic generation, sum frequency generation, difference frequency generation, and optical Kerr effect.

Near-field optical signals can be enhanced by the nanoparticles of the present invention, be they non-aggregated nanoparticles and/or aggregated nanoparticles. By doping the material to be detected onto a medium that comprises the nanoparticles, near-field optical signals are enhanced. In the method where the light signal is detected through an optical fiber, the medium can be instead deposited onto the input end of the optical fiber. Furthermore, the microcavity of the present invention can enhance near-field optical spectroscopy of a material when that material is located in the vicinity of the microcavity. By combining the doped medium with the microcavity and locating the medium in the vicinity of the microcavity, near-field optical spectroscopy can also be enhanced. In the case where the light signal is detected through the optical fiber, the medium could be instead deposited onto the input end of the optical fiber [rather than doped onto the medium].

A primary object of the present invention is to enhance optical emission of molecules by placing such molecules on or near fractals, and locating them within or on a surface of a microcavity for still further enhancement.

Another object of the present invention is to enhance optical emission of nano-sized particles, quantum dots, by placing the nanoparticles on or near fractals located within or on a surface of a microcavity.

A primary advantage of the present invention is the observed enhanced optical emission and lasing of molecules, or nanoparticles, placed on or near fractals located within or on a surface of a microcavity.

Another advantage of the present invention is the observed surface-enhanced Raman scattering, and other linear and non-linear optical processes of molecules, or quantum dots, placed on or near fractals located within or on a surface of a microcavity.

Another advantage of the present invention is the enhanced optical emission of dye molecules placed on or near fractals located within or on a surface of a microcavity.

Other objects, advantages and novel features, and further scope of applicability of the present invention will be set forth in part in the detailed description to follow, taken in conjunction with the accompanying drawings, and in part will become apparent to those skilled in the art upon examination of the following, or may be learn ed by practice of the invention . The object s and advantages of the invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating a preferred embodiment of the invention and are not to be construed as limiting the invention. In the drawings.

DESCRIPTION OF THE PREFERRED EMBODIMENTS

(BEST MODES FOR CARRYING OUT THE INVENTION)

Figure 1:
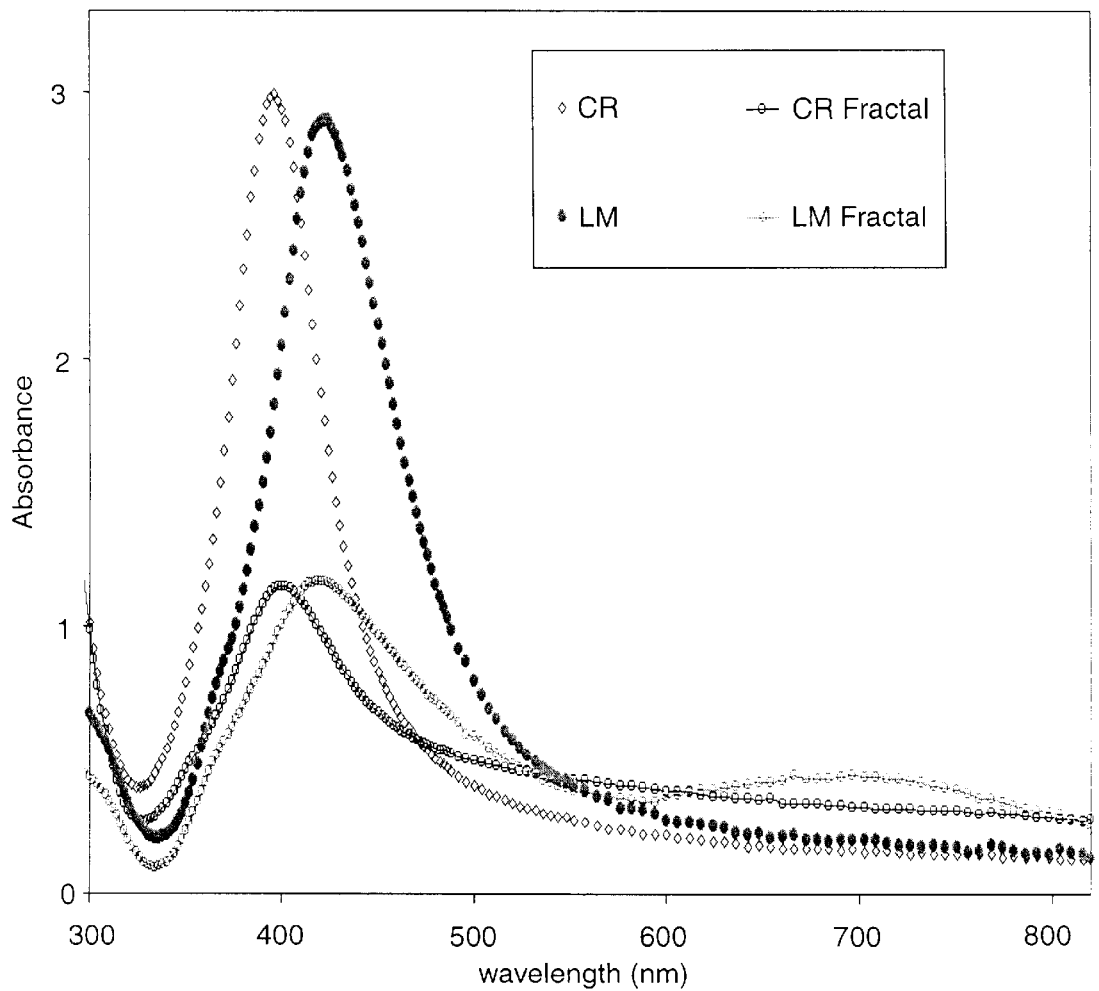
FIG. 1 is an absorption spectrum of a typical bright-yellow colloid solution prepared by the Creighton method, shown by curve CR, and an absorption spectrum prepared according to the Lee and Meisel methods, curve LM, showing the respective absorption spectra of the two.

In the present invention, nanoparticles—both non-aggregated and aggregated as fractals, microcavities, and fractal/microcavity composites are used to produce various linear and nonlinear optical effects including surface enhanced Raman scattering (SERS), lasing, and surface-enhanced hyper Raman scattering (SEHRS). In general, a light source such as a laser excites a medium comprising nanoparticles, either non-aggregated nanoparticles and/or aggregated nanoparticles. (Fractals are made up of aggregated nanoparticles, preferably 10 nanoparticles.)

Preferably each nanoparticle is of an average diameter that is less than the optical wavelength of interest, and the microcavity has an exterior dimension that is at least twice that of the optical wavelength of interest. Preferably the fractals have a dimension that is less than the embedding space. The nanoparticles are located in the vicinity of a microcavity to further enhance optical emission. To be in the vicinity of the microcavity, the medium can be within the boundary of the microcavity or within a lightwave length of the surface. Either solid or hollow microcavities can be used and the medium can be located on a surface, or contained or embedded within. The medium is typically contained within a liquid suspension, a gel matrix, or a solid matrix. A variety of applications for the use of nanoparticles and/or microcavities are provided.

The nanoparticle medium can be a metal such as silver, gold, platinum, copper, aluminum, or magnesium; semi-metal such as graphite; or semiconductor such as Group IV, Group III-V, and Group II-VI semiconductors. Optically active organic and inorganic molecules can be adsorbed on a surface of the nanoparticles, or located within the light wavelength of the surface of the nanoparticles. When discussed herein the adsorbed species can be any molecules, and the invention is not to be limited to the laser dye or sodium citrate molecules discussed below. Various types of laser dyes can be used such as xanthene, coumarin, pyrromethene, styryl, cyanine, carbon-bridged, naphthofluorescein-type, acridone, quinalone derivative, p-terphenyl, p-quaterphenyl, and 9-aminoacridine hydrochloride dyes. Bacterium, inorganic and organic compounds, nucleic acid, quantum dots, quantum wires and such can also comprise the adsorbed species.

The present invention is also a method of doping a material onto the nanoparticle medium, so that the optical emission of a material can be enhanced. These materials can include anything from a single molecule to a plurality of molecules, a nanocrystal, a solid matrix, DNA, DNA fragments, amino acids, antigen, antibodies, bacteria, bacterial spores, and viruses.

Experiments revealing the enhanced optical emissions gained with the present invention will now be described.

Preparation of Silver Colloid Solution

Silver colloid and silver fractal solutions were prepared using the Creighton method or the Lee and Meisel method. Such solutions can of course be prepared through other known means. All glassware used for the preparation of such solutions were soaked in sulfur-chromic acid for at least two hours, and thoroughly rinsed several times with deionized water. The preparation of silver colloid and silver fractal solutions also requires that the glassware not have any physical damage, such as scratches, because any contamination or scratch on the glassware would cause the unwanted rapid aggregation of colloid particles.

The colloidal preparative methods are based on the reduction of aqueous silver nitrate solutions. The characteristics, such as uniform size and spherical shape, and stability of the prepared colloid solutions is dependent on the reduction agents used and the rate of reduction. The reduction rate was controlled by varying the temperature of the reacting solutions. Both methods achieve the best results by applying vigorous stirring during the initial stages of the reaction. Absorption spectroscopy was used to characterize the prepared colloid solutions.

The resulting colloid solutions and fractals were characterized using a Hitachi H-7000 transmission electron microscope (TEM) with a magnification up to 100,000. Specimens for TEM were prepared by placing a small volume approximately 2 to 5 $\mu$l, on a 3 mm diameter carbon-coated membrane supported on a copper grid. A similar method was used for preparation of scanning electron microscopy (SEM) samples.

Creighton's Method

A $1 \times 10^{-3}$ M aqueous solution of silver nitrate $AgNO_3$ (20 ml) at 0° C. was added drop-wise to a $2 \times 10^{-3}$ M sodium borohydride solution, $NaBH_4$ (60 ml) at 0° C. This method generally produced uniform, spherical colloid particles with an average diameter of about 15 nm. A clear yellow color appeared immediately after mixing both solutions. Vigorous stirring was required during the initial mixing process, approximately 5 minutes, followed by slow and gentle stirring for approximately 20 minutes. The solution was transferred to a clean, brown glass bottle, and permitted to come to room temperature (approximately 4 to 5 hours). The solution was then cooled in a refrigerator until needed. Because optical responses depend on the size and shape of the colloid particles, it is necessary that the colloid solutions have a long shelf life. The shelf life, i.e., the non-aggregation stability of these solutions, were monitored by visible absorption spectra (the color changes as fractals become larger) and TEM micrographs. This data revealed that a well-prepared and adequately stored solution remains unchanged for approximately one year.

FIG. 1 shows the absorption spectrum of a typical brightyellow colloid solution prepared by the Creighton method, curve CR, with a relatively sharp peak at 400 nm. The location of this peak is characteristic of the average size (15 nm) of the particles, and the width corresponds to the distribution of the particle size in the solution. The narrower the width of the peak, the narrower the size distribution.

Lee and Meisel Method

The method of Lee and Meisel was also used to prepare colloid solutions. A 90 mg sample of silver nitrate, $AgNO_3$, was dissolved in 500 mL of distilled water. The solution was heated to reflux, and 10 mL of a 1% solution of sodium citrate added drop-wise with vigorous stirring. The solution was refluxed for 60 to 90 minutes, that is, until the color of the solution gradually changed from transparent to milky yellow to greenish yellow. The temperature of the heating bath was maintained at approximately 125° C. during the reflux period. This procedure ensured the formation of silver nanoparticles (monomers) with an average diameter of 25 nm. Thus, the average size distribution of the nanoparticles were larger than the nanoparticles prepared by the method of Creighton. The solution was permitted to cool to room temperature, after which the solution was poured into a brown glass bottle and placed in a refrigerator. Visible adsorption spectra of non-aggregated silver colloid solutions prepared by the Lee and Meisel method exhibited a single resonance feature of approximately 420 nm with a width of 80 nm as shown in FIG. 1, curve LM.

Preparation of Fractals

Regardless of the preparation method used, the colloid solutions were quite stable for a reasonably long period of time. However, upon the addition of an adsorbate, such as a fumaric acid (approximately 0.03 M) or a solution of a sodium chloride (approximately 0.5 M), to the "monomer" colloid solution, aggregation of colloidal nanoparticles into fractal clusters was observed. Each fractal was estimated as containing approximately $10^3$ monomers. A typical cluster-cluster aggregation process occurs wherein some fractals comprise more than $10^3$ particles and some fractals comprise smaller clusters on the order of 10 to 300 particles.

Electron microscopic analysis of these aggregates demonstrates that they possess a fractal structure with the fractal dimension D ~1.77; cluster-cluster aggregation of particles result in D=1.78 by computer simulations. The fractal dimension was obtained by counting the number of monomers within a given region for several different size fractal clusters consisting of 500 to 3,000 particles, and comparing it to the theoretical formula, $N=.(R_C/R_0)^D$ of the scaling theory, where N is the number of monomers in a gyration radius $R_C$ of a fractal cluster, and $R_0$ is a constant of length of the order of the minimum separation between particles. The measured fractal dimension is within 1% of the theoretical one.

Aggregation of the nanoparticles into fractals can be inferred by observing the color change of the solutions from yellow to orange, to pink, to blue and finally to gray as well as the appearance of a broad band in the absorption spectrum extending toward the longer wavelengths. The average lifetime before the precipitation of the aggregates from the colloid solution is about two hours.

Fractal/Microcavity Composites

Fractal/microcavity composites comprise aggregated nanoparticle fractal solutions in various stages of aggregation contained within a quartz tube. Preferably, a hollow, fused quartz, cylindrical microcavity was used to investigate the nonlinear behavior of the fractal/microcavity composites. The outside diameter of the microcavity tube was approximately 1 mm and the inside diameter was approximately 0.7 mm. The invention is not limited to cylindrical microcavities, and alternative geometries and sizes are also possible, for example cylindrical microcavities, spherical microcavities, spheroidal microcavities, polyhedral microcavities, and optical wave guide microcavities can be used in accordance with the invention. Because of the small size of the quartz tube, the colloid solutions, both before and after aggregation, were introduced by capillary action.

Figure 2A:
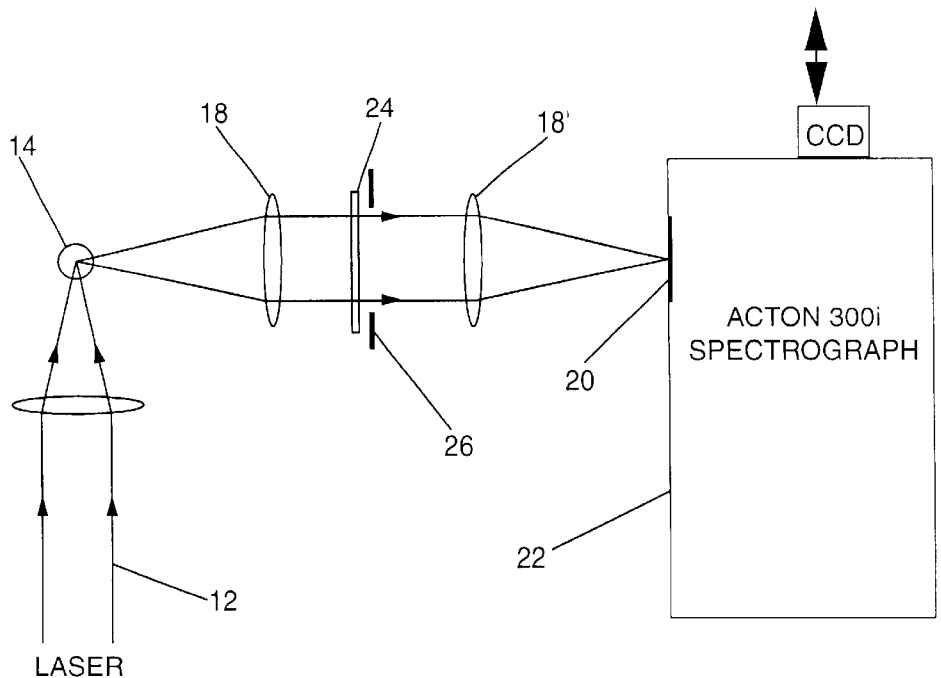
FIG. 2a shows a diagram of the laser optical bench used to measure optical enhancements obtained using the present invention.

Attention is now turned to FIG. 2. FIG. 2a shows a diagram of the laser optical bench used to measure the optical enhancements of the fractal/microcavity. The light source of the invention can be a laser and preferably emits light of wavelengths between approximately 200 and 100,000 nanometers, more preferably between approximately 300 and 2,000 nanometers. The light source power can be anywhere from approximately 1 nanowatt to 100 watts, which can be provided by many types of lasers. In FIG. 2a, one of several continuous wave laser beam light sources, e.g. a He-Ne laser ($\lambda_L$=543.5 nm, 0.75 mW; $\lambda_L$=632.8 nm, 85 mW), or an Argon ion laser ($\lambda_L$=488 nm, 10 mW; $\lambda_L$=514.5 nm, 50 mW) were focused on microcavity 14 containing sample solutions, and used as the pump beam 12. In order to avoid any confusion on data collection due to plasma lines from a laser source, a laser filter with a bandwidth less than 10 nm was used. Pump beam 12 (approximately 2 mm in diameter for a green He-Ne laser and Argon ion laser, 5 mm for a red He-Ne laser) was focused on microcavity 14 by 75 mm focal length lens 16; focal plane beam diameters were 70 $\mu$m, 35 $\mu$m and 50 $\mu$m for Argon lasers $\lambda_L$=488 and 514.5 nm), and for He-Ne lasers ($\lambda_L$=543.5 nm and $\lambda_L$=632.8 nm). The polarization of all pumping sources was vertical along the axis of microcavity 14, and the output radiation was collected at a fixed angle of 90 degrees to the incident radiation by two identical lenses of 100 mm focal length, 18 and 18'. The combination of two identical lenses 18 and 18' makes it possible to collect 1:1 images of excitation spots around a cylindrical microcavity in entrance slit 20 of a 30 cm focal length Acton SpectraPro-300i spectrograph 22.

Figure 2B:
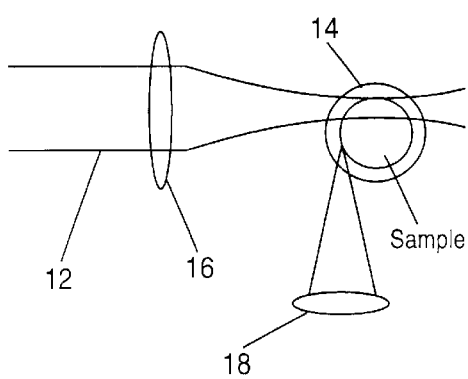
FIG. 2b shows an alternative configuration to that of FIG. 2a when exciting MDRs in the cylindrical microcavity for lasing and hyper-Raman scattering measurements.
Figure 2C:
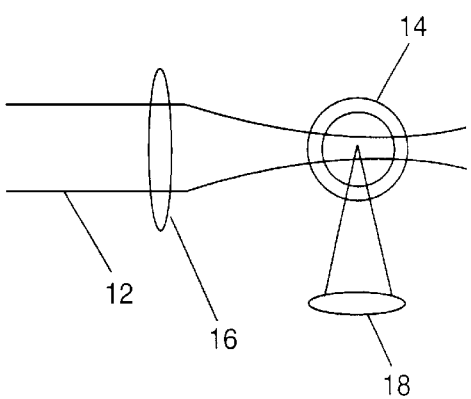
FIG. 2c shows an alternative configuration to that of FIG. 2a when collecting enhancement measurements due only to fractal structures instead of MDR.

Configuration FIG. 2b was used when MDRs were to be excited in the microcavity for both lasing and hyper-Raman scattering measurements. In each case, the position of pump beam 12 was carefully adjusted on the microcavity to excite fractals doped with optically active media such as Rhodamine 6G (R6G) dye molecules for lasing measurements, or sodium citrate molecules for normal and hyper-Raman scattering measurements. The position of pump beam 12 shown in FIG. 2c was used to collect enhancement measurements due only to fractal structures and not the MDR. The ratio of the spectral responses, i.e., with and without the microcavity, is then used to estimate the enhancement factors associated only with the resonant microcavity.

Spectroscopic measurements were performed using an intensified charge coupled device (ICCD) camera (27 $\mu$m. 564×384 pixels with Princeton ST-138 controller) mounted to the SpectraPro-300i spectrograph. Two gratings installed in the spectrograph were a 300 groove and an 1800 groove per millimeter grating blazed 500 nm, which provided a spectral resolution of 0.12 nm and 0.04 nm, full width at half maxima (FWHM), respectively. The coarse 300 groove grating was used to obtain a broader range of spectral data, approximately 60 nm around orange range. The finer 1.800 groove grating was used to obtain 10 nm or less ranges such that the details of spectra, for example, using this grating, the mode spacing of MDRs could not be obtained.

A set of filters 24 were placed between lenses 18 and 18'. A set of color filters (long pass filters), a few short pass filters, a set of neutral density filters (Oriel) and laser notch filters with optical density 6 at pump laser wavelength were used. For hyper-Raman scattering measurements, a set of metallic density filters (Oriel) ranging from optical density 0.1 to 3 around 500 nm (these filters have a slightly higher optical density in the UV region from 200 to 400 nm) were used. UV-enhanced silica lenses to collect outcoming optical signals were also used. Since optical signals emitted from a microcavity are quite different from one location to another, careful and consistent focusing onto entrance slit 20 is required in order to obtain consistent optical enhancements. Positions of both collecting lenses 18 and 18' were controlled with precision micrometers in order to achieve optimal and consistent optical enhancements from one measurement to another. A set of iris diaphragms shown generally at 26 placed along the collecting path to slit 20 ensured the alignment of the lenses, and eliminated unwanted scattering noises. The width of entrance slit 20 also affected the characteristics of the enhanced optical response. The optimum size of entrance slit 20 is between approximately 10 $\mu$m and 50 $\mu$m.

Figure 3:
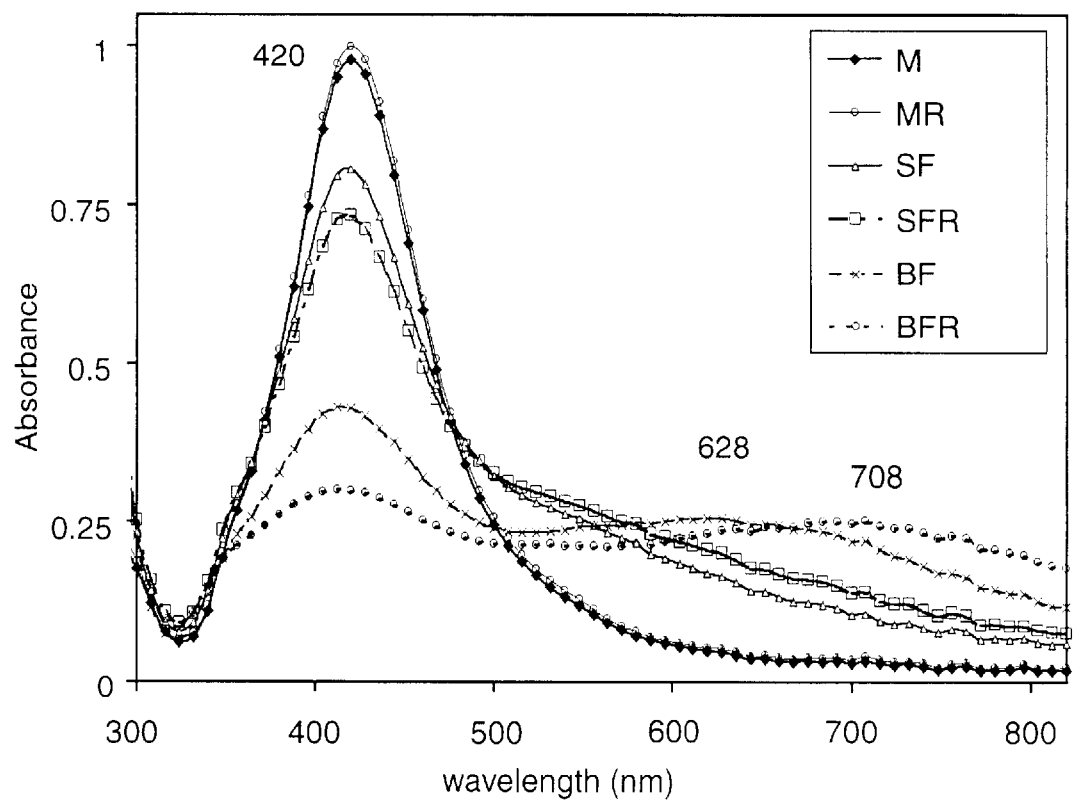
FIG. 3 shows absorption spectra of freshly prepared silver colloid solutions and corresponding fractal aggregates.

Attention is now turned to FIG. 3. Absorption spectra of freshly prepared silver colloid solutions containing non-aggregated particles (M) and non-aggregated particles doped with ($5\times10^{-7}$ M) Rhodamine 6G dye molecules (MR) are shown in FIG. 3. The corresponding fractals produced were: small aggregates produced with fumaric acid (SF); large aggregates produced with fumaric acid (BF); small aggregates produced with fumaric acid and doped with R6G (SFR); and large aggregates produced with fumaric acid and doped with R6G (BFR). As shown in FIG. 3, the addition of the dye molecules resulted in a very small change in the absorption spectra, which indicated that the amount of R6G used to optically determine the amount of enhancement caused by the fractal/microcavity composite does not initiate aggregation of the silver colloid particles. Instead, fractals were produced by adding a small amount of an acid solution, such as 0.03 M fumaric acid, citrate acid and so on, or a salt solution. The absorption spectra containing the adsorbate is not significantly dependent upon what adsorbate is used so long as a proper volume ratio for each adsorbate remained constant.

As R6G in methanol is added to the solution of aggregates (SF and BF), an increase in aggregation beyond that initiated by the addition of an adsorbate is observed. See spectra SFR and BFR in FIG. 3. In other words, adding a small amount of R6G, without fumaric acid, to the fresh colloidal solution does not initiate aggregation (see MR), but does promote further aggregation if the acid was initially added (see SFR and BFR).

The order of adding the various components, e.g., acid to dye or dye to acid, does not result in any appreciable difference in the observed absorption spectra, however the lifetime of the samples was affected. For example, when R6G is added prior to the addition of the acid adsorbate a shorter lifetime, and increased rate of fractal precipitation, was observed. Although optical enhancement is similar in both cases, it is preferred that the R6G be added to the adsorbate-produced fractals because the lifetime of the fractal solutions is greater, thus providing more time to record optical response measurements. Also, optimal optical enhancements were observed when R6G was added to a solution approximately thirty minutes after the adsorbate was added.

Lasing of R6G Doped on Fractals in Microcavities.

Lasing experiments were performed with R6G dye/fractal/microcavity composites. A small amount of a $10^{-4}$ M R6G solution in methanol was added to a silver fractal solution; the resulting dye concentrations in the samples ranged from $10^{-5}$ to $10^{-8}$ M. Cylindrical microcavities were fabricated from cylindrical quartz tubes having an inner diameter of 0.7 mm, and an outer diameter, 1.0 mm. The fractal/dye samples were prepared about thirty minutes before the lasing measurement. It is proposed that some time is needed for the dye molecules to become adsorbed on the fractals.

Figure 4:
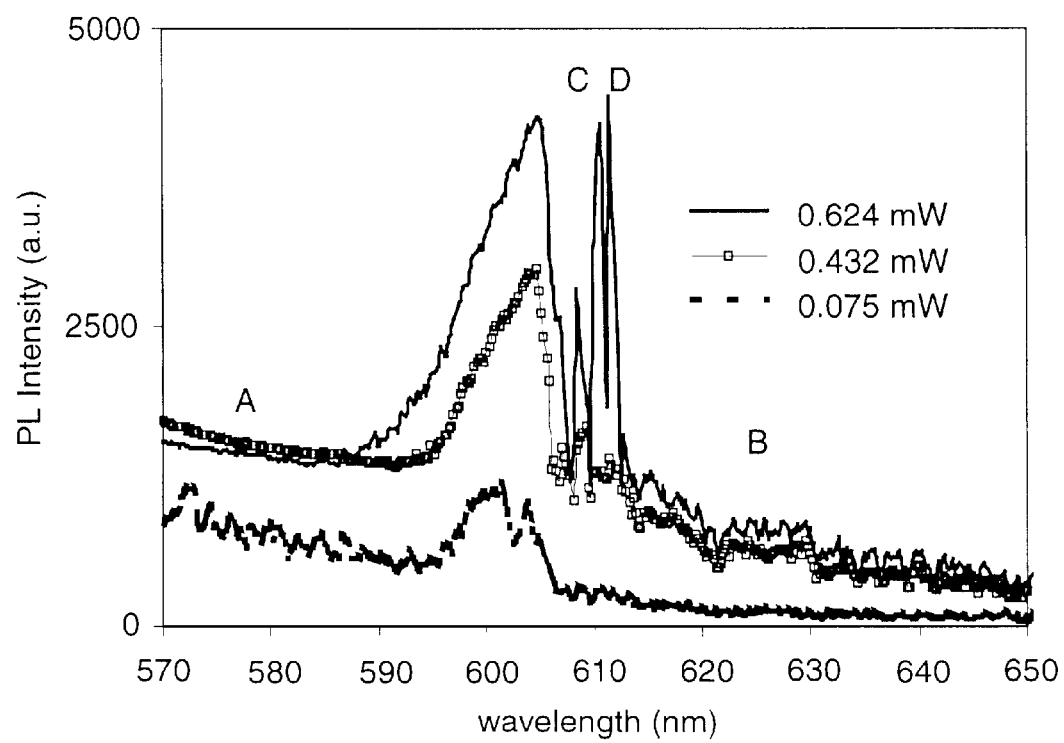
FIG. 4 shows photo luminescence (PL) spectra at different intensities of the pump beam from dye molecules doped on silver particles, wherein luminescence spectra are denoted at A and B, and peaks due to lasing are denoted at C and D.
Figure 5:
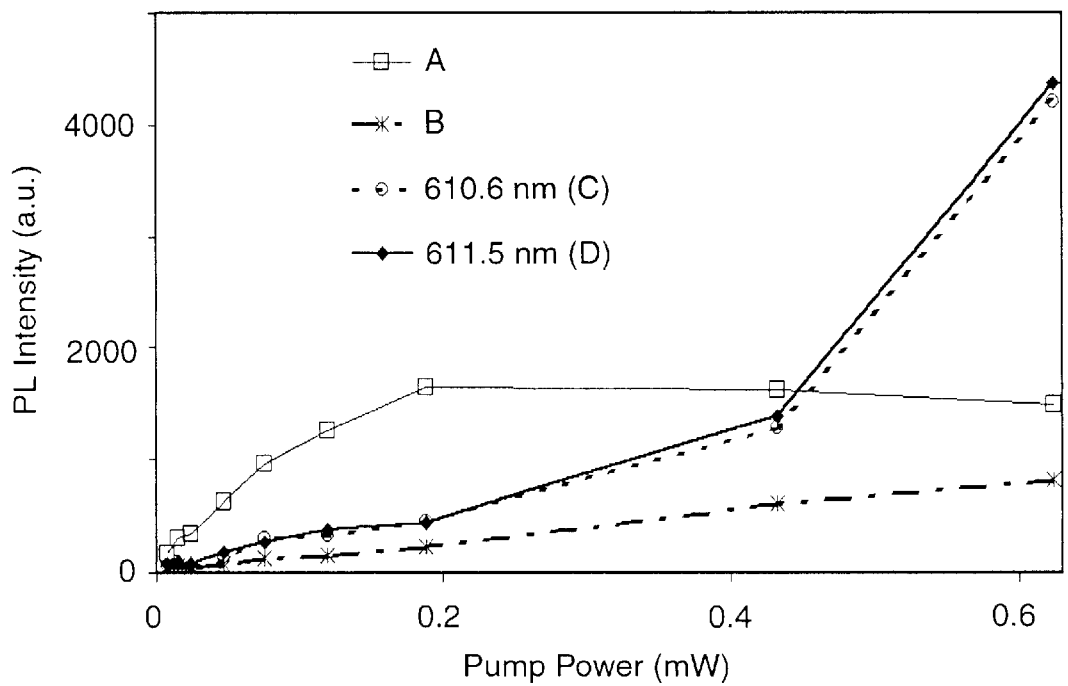
FIG. 5 shows A, B, C, and D of FIG. 4 as a function of pump power.
Figure 6:
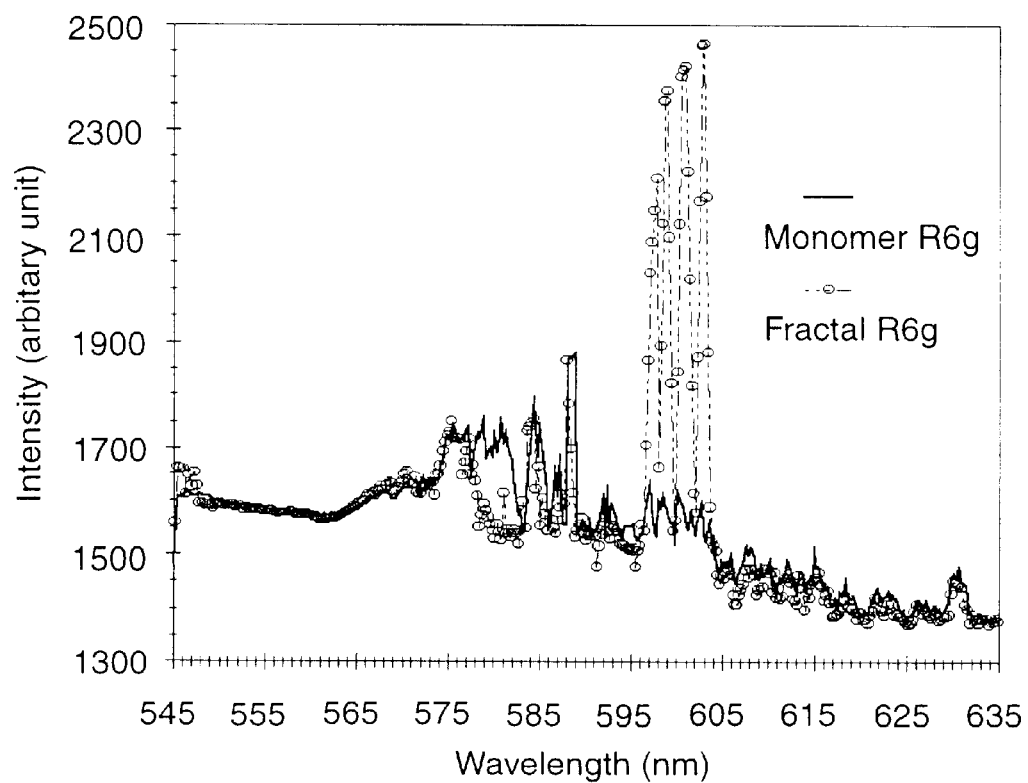
FIG. 6 compares the difference between enhancements in Rhodamine 6G dye molecules adsorbed on silver monomer and fractals.

The emission intensity of different spectral components as a function of the pump intensity were measured. Attention is now turned to FIG. 4. FIG. 4 shows the photoluminescence spectra at different intensities of the pump beam (He-Ne laser; $\lambda_L$=543.5 nm). Luminescence spectra from dye molecules doped on silver particles are denoted as A and B. Peaks C and D corresponds to lasing. Turning to FIGS. 5 and 6; FIG. 5 shows the threshold dependence of the lasing lines and FIG. 6 shows the actual lasing spectrum. For comparison to FIG. 4, FIG. 5 shows the threshold effect for lasing (C and D) as well as the pump power dependence of spectral components A and B. Although a sample containing large fractals was used (1~2 μm size for approximately 3,000 monomers in an average fractal), the spectrum for low intensity irradiation, which is the bottom dashed line in FIG. 5, is quite similar to that of monomers. Note that the luminescence signal from non-aggregated monomers shown in FIG. 6 is quite similar to the bottom spectrum in FIG. 5.

The dependence of luminescence intensity on pump power is linear for low excitation intensities for all spectral components, as shown by FIG. 5. However, when the pump intensity exceeds some critical value in the range between 20 and 50 W/cm$^2$, some peaks grow dramatically, exhibiting a lasing threshold dependence as shown in FIGS. 4 and 5. The threshold power for the $\lambda_L$ which 543.5 nm He-Ne pump laser is as small as $2\times10^{-4}$ W. It is noteworthy that the R6G concentration was only $5\times10^{-7}$ M which corresponds to a maximum of 230 dye molecules per nanoparticle if all dye molecules adsorbed on the surface of silver particles, which is three orders of magnitude lower than that for conventional dye lasers with an external cavity in the absence of fractals, and three orders of magnitude less than that for a micro-droplet laser without silver fractal aggregates. In contrast, the minimum R6G concentration required for lasing with fractals contained within microcavities is as low as $10^{-8}$ M. Also, the threshold pump intensity used with fractal/microcavities was approximately three orders of magnitude less than a conventional dye laser. These results indicate that the lasing effect is due to dye molecules adsorbed on the surface of silver aggregates.

Therefore, surface-plasmon-enhanced radiation effects in fractal/microcavity composites lead to dramatic lasing effects. This conclusion is supported by the fact that increasing the R6G concentration up to $10^{-5}$ M does not result in additional growth of the lasing peak intensities. In such cases, the greater dye concentration is apparently too large to be adsorbed onto the silver particles, and the additional dye, remaining in solution as free molecules, does not effectively contribute to lasing. Therefore, the presence of metal colloid particle fractals contained within the resonant microcavity is the main contribution to linear and nonlinear optical enhancement.

The placing of R6G dye in a microcavity leads to $10^3$ to $10^5$ enhancement of the dye photoluminescence. By adding non-aggregated silver colloidal particles to the dye solution in a microcavity, further (multiplicative) enhancement is obtained, varying between $10^2$ and $10^3$. Finally, aggregation of the colloidal particles into fractals in the microcavity results in an even greater enhancement, which can be as large as $10^4$. The resultant (multiplicative) enhancement obtained was in the range between $10^9$ and $10^{12}$, on average, and several orders of magnitude more, in the fractal hot spots.

In order to compare the enhancement quantitatively, a set of neutral density filters, with a total optical density between 2 and 3, were placed before the entrance slit of a spectrograph in the case of large fractal measurements. As shown in FIGS. 5 and 6, the photoluminescence of non-aggregated silver colloid particles (monomers) is quite similar to the dashed spectrum, 0.075 mW, in FIG. 4. Thus, the overall emission enhancement resulting from adsorption of the dye molecules on the surface of the fractals in a microcavity can vary between $10^9$ and $10^{12}$. FIG. 6 reveals the difference of the enhancements in Rhodamine 6G dye molecules adsorbed on silver monomers and fractals. As shown, the fractal spectrum (dashed line) was reduced by a factor of $10^3$ because an optical density 3 filter was placed in the path of the collection optics.

The lasing effect depends on both the spontaneous emission rate of the adsorbed dye molecules, as well as the enhancement created by the pump and the generated beams within the microcavity. The spontaneous rate of a particle in a resonator differs from the rate in a vacuum, i.e., the Purcell effect, because the density of photon states is modified by the resonator. The spontaneous emission rate Γ is proportional to the photon density of states ρ(ω), and gives the enhancement factor (Purcell factor $F_\rho$) in a resonant cavity compared to the emission in vacuum as:

$$F_p = \frac{\Gamma}{\Gamma_0} \sim Q\left(\frac{\lambda}{L}\right)^3, \qquad (1)$$

where the subscript 0 denotes the vacuum and L denotes the length of the microcavity. If optically active molecules, such as dye molecules, are adsorbed on the surface of a fractal, additional strong enhancement can be achieved due to enhancement of the zero-point, or vacuum, field fluctuations in fractals. Thus, the combined effect of a microcavity ("conventional" Purcell effect) and the local-field enhancement of zero-point fluctuations due to the plasmon modes in fractals can result in a dramatic modification of the spontaneous emission rate.

With the assumption of low concentration of fractals in the cavity, the surface-enhanced Purcell factor $F^{SE}$ for a dye/fractal/microcavity composite is a product of $F_\rho$ and the local-field factor:

$$G = <|E(r)|^2 > / |E_0|^2 \text{ as} \qquad (2)$$

$$F^{SE} = \frac{\Gamma}{\Gamma_0} = \frac{\langle|d|\rangle^2}{|d_0|^2} \frac{\rho(\omega)}{\rho_0(\omega)} \sim GQ\left(\frac{\lambda}{L}\right)^3. \qquad (3)$$

Although the cylindrical microcavity used is too large to observe the conventional Purcell effect, multiplicative enhancements of lasing results from the "classical" enhancement of the pump and generated beams as well as from the "quantum" factor characterizing the predicted modification of spontaneous emission due to the localized plasmon modes in fractals. See equation (1) above.

Photo Initiated Aggregation of Colloid Particles

A pronounced time-dependent effect was observed when a fresh silver colloid solution was irradiated with a CW, 543.5 nm green He-Ne pump laser at a power of 0.75 mW. Initially, the solution contained non-aggregated silver particles doped with Rhodamine 6G dye molecules. The overall concentration of R6G dye in the solution was $5\times10^{-7}$ M, which is not enough to generate strong lasing emission in a colloid solution. However, after approximately thirty minutes of irradiation, during which time only extremely weak luminescence was observed, strong lasing emission spontaneously appeared from the microcavity.

It is proposed that this time-dependent lasing effect is due to photo-stimulated aggregation, whereby initially non-aggregated, or weekly aggregated, silver colloidal particles undergo in situ aggregation in response to irradiation by a He-Ne pump laser. In such a case, the aggregated particles, or fractals, are "pulled" into high-field regions of the MDRs as a result of electromagnetic gradient forces, and resonant multiplicative enhancement is sufficient to lower the lasing threshold to the level provided by the He-Ne pump laser. As a result, the measured overall enhancement of the light emission due to the combined effects of the resonant microcavity and fractals is between approximately $10^{10}$ and $10^{12}$.

During the photo-initiated aggregation experiment several different procedures were tried in order to investigate how the pump beam influenced aggregation of the colloid solution. What was observed was that the lasing effect was dependent upon the localized position of the light source, or pump beam, on the resonant microcavity. As the pump beam was moved approximately 100 $\mu$m away from the initial position where dramatic lasing emissions were observed, the lasing emission disappeared. However, the lasing emissions reappeared at the new position after about forty minutes. After blocking the pump beam for approximately thirty minutes a strong lasing emission at both the new and the original positions were observed. Several measurements confirmed that the approximate time needed for the nano-composites to migrate and aggregate was between approximately twenty to thirty minutes. The lasing emissions last between approximately one to two hours. After which the silver aggregates grow too large and precipitate out of the solution. In fact, even without the pump beam, an initial colloidal solution becomes transparent, and precipitated aggregates become visible at the bottom of the microcavity after several hours. This indicates that ambient room light is sufficient to photo-aggregate colloidal particles in the microcavity, because fresh colloid solutions in a microcavity can be stored in the dark for up to approximately two months.

Morphology Dependent Resonance with Fractals in Microcavities

The enhancement factor for Raman scattering of a tractal solution was found to be $10^5$ to $10^7$. However, when that same solution was placed within a microcavity, an additional enhancement factor on the order of $10^3$ to $10^5$ was observed. This demonstrates the unique potential of fractal/microcavity devices in the development of ultra-low threshold microlasers, of linear and nonlinear optical devices for photonics, as well as new opportunities of micro-analysis, including spectroscopic studies of single molecules. Several applications in particular are described in the examples below.

Elastic scattering of a laser beam passing through an outer edge of an empty cylindrical tube exhibits well-defined, MDR angular structure. In contrast, when the beam passes through an inner edge of an empty tube, the MDR intensity is significantly less. Consequently, optimal enhancements were observed using inner edge illumination geometry because it provides the effective optical excitation of fractals within the cavity and their coupling to the MDRs. Filling the tube with a colloidal solution resulted in strong elastic scattering with a clearly resolved MDR angular structure. This indicates that light scattering by colloidal particles facilitates trapping of the radiation in the MDR cavity modes. Elastic scattering by fractals and monomers also contributes to output-coupling of radiation from microcavity MDRs. Scattering, together with absorption, decreases the quality-factor, $Q^{-1}$, of the cavity modes according to $$\frac{1}{Q} = \frac{1}{Q_A} + \frac{1}{Q_{SS}} + \frac{1}{Q_{SV}} \tag{4}$$

where $Q_A^{-1}$, $Q_{SV}^{-1}$, and $Q_{SS}^{-1}$ are losses due to absorption, volume scattering, and surface scattering, respectively.

Figure 7:
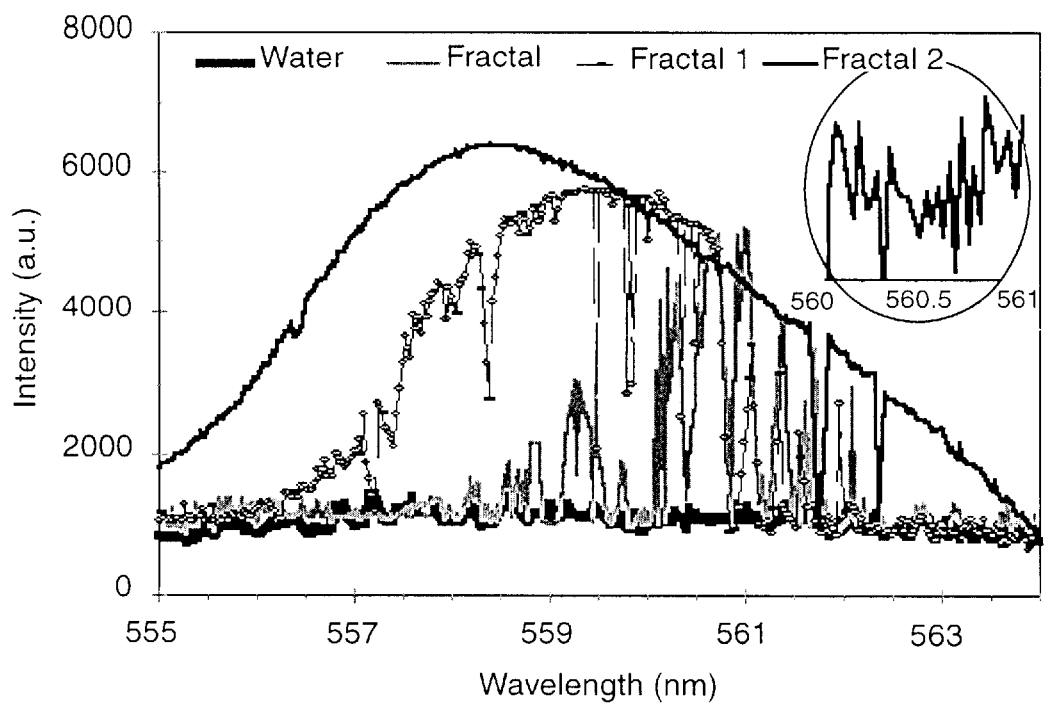
FIG. 7 shows the luminescence spectrum of water and the corresponding fractal enhanced spectra of Rhodamine 6G dyes doped on silver colloid fractals within a microcavity.

FIG. 7 contrasts the luminescence spectrum of a dye solution ($5\times10^{-7}$ M), with and without the presence of fractals in a microcavity ($\lambda_L$=514.5 nm excitation; Argon-ion laser). The volume ratio of water and methanol is 200:1 in both cases. A weak, broad luminescence band is observed with a maximum near 560 nm and a FWHM of 30 nm without colloidal particles or fractals in a microcavity under the $\lambda_L$=514.5 nm excitation. The presence of fractal aggregates of silver colloidal particles results in large peaks in the spectrum with the mode spacing of 0.066 nm. See insert of FIG. 7. This spacing is close to, but somewhat less than the calculated inter-mode spacing, $$\Delta\lambda = \frac{\lambda}{2\pi a} \frac{\tan^{-1}(\sqrt{n^2-1})}{\sqrt{n^2-1}} \tag{5}$$

which becomes approximately 0.076 nm for a quartz, refractive index n=1.46, cylinder of radius a=0.5 mm and water as host medium ($n_h$=1.33).

The emission spectrum with 10 mW Argon ion laser pumping of an aggregated silver colloid solution with a R6G concentration of $5\times10^{-7}$ M, differs dramatically from that of the pure R6G solution. A heavy, gray-colored curve denoted "Fractal" in FIG. 7 illustrates the huge increase in peak intensities in a narrow spectral region centered near 561 nm with a bandwidth of approximately 3 nm. The mode structure in this spectral range is approximately the same as for a pure dye solution in a cavity with no fractals. This indicates that the presence of fractals in a microcavity does not appreciably perturb the cavity MDRs. Fractal, Fractal 1, and Fractal 2 spectra in FIG. 7 represent spectra taken with an optical density 2 filter in place and for different CCD detection exposure times, 1, 2, and 3 seconds, respectively. "Water" signals are obtained without the optical density 2 filter, and with 1 second exposure time of the CCD. Simple scaling gives a $10^4$-time enhancement caused by the presence of fractals doped with dye molecules. Thus, the maximum optical enhancement around the 561 nm region may reach up to $10^6$ or $10^7$.

Surface-Enhanced Raman Scattering of Sodium Citrate

SERS spectra from sodium citrate molecules adsorbed on silver fractal aggregates were obtained under two experimental geometries where MDRs either were, or were not, excited. See the geometries shown in FIGS. 2b and 2c, respectively. Of greater interest is the coupled, multiplicative enhancement factor caused by both fractals and microcavities. By comparing Raman signal levels from sodium citrate adsorbed on silver colloid aggregates with a high concentration sodium citrate solution without colloidal particles, a SERS enhancement of $10^5$ to $10^7$ was observed for the fractal solution. Thus, by adding the SERS enhancement due to the resonant microcavity, the total average enhancement of a fractal/microcavity composite is estimated to be approximately between $10^8$ to $10^{12}$. This large enhancement occurs in spite of the presence of fractals in a microcavity which is expected to decrease its quality-factor as a result of absorption and scattering. Further, since the optical excitations are localized in small nanometer-size hot spots, the local enhancement in these hot spots is expected to exceed the average enhancement factor by 5 to 6 orders of magnitude.

As a result, the maximum local SERS enhancement can be as large as $10^{13}$ to $10^{18}$. These enhancement factors are comparable with, and exceed, the previously reported local enhancements for single molecule SERS of $10^{12}$ to $10^{15}$. Thus, by placing fractal nanostructures in a microcavity or coating them on the outer surface of a microcavity new possibilities exist for optical micro-analysis and detection. In addition, the invention provides for the spectroscopic investigation of lasing and nonlinear optical effects of single molecules, or quantum dots, including semiconductor quantum dots.

Figure 8:
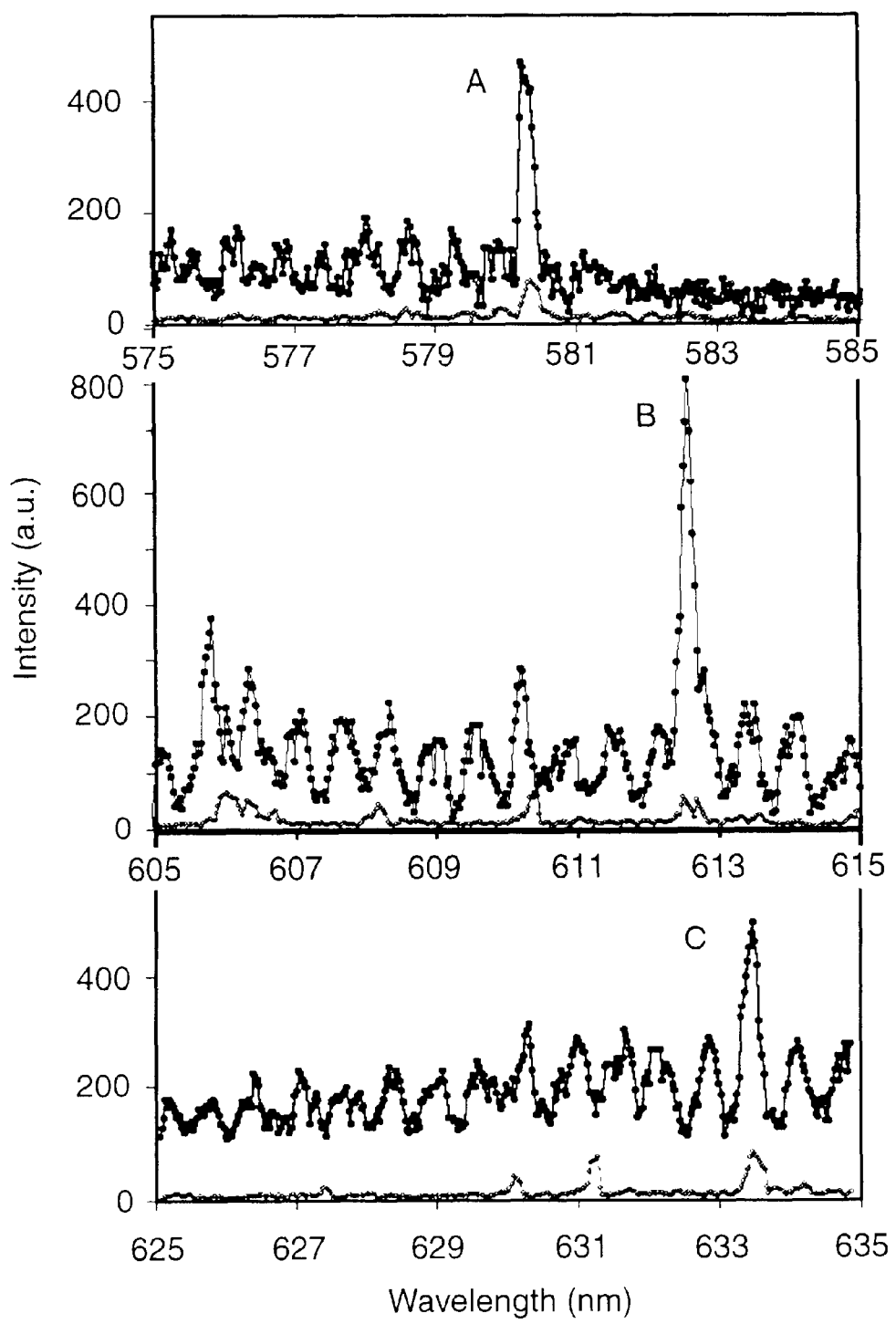
FIG. 8 shows microcavity Raman spectra of aggregated silver monomers without Rhodamine 6G dye under Helium Neon laser excitation.

FIG. 8 shows the difference in microcavity spectra of non-aggregated silver monomers without R6G dye (lower trace), and with fractal aggregates containing a $5\times10^{-7}$ M dye solution (upper trace) under $\lambda_L$=543.5 nm He-Ne excitation. FIG. 8 shows three fragments of this spectrum between 575 nm and 635 nm. The top solid-lines represent spectra of the dye-doped fractals of silver colloid particles; the bottom dashed lines show spectra of non-aggregated colloidal particles without dye molecules doped. Addition of a sodium citrate solution (0.1 M concentration with 1/200 volume ratio) resulted in aggregation of the silver monomers. Analogously to the case of Argon-ion laser excitation, a set of peaks whose minimal spacing is approximately equal to the intermode spacing of the cylindrical microcavity was observed. The observed width of the peaks essentially corresponds to the instrumental width, so that the real peak width is actually smaller than the measured value $\delta\lambda$=0.04 nm. This allows one to estimate a lower bound for the quality factors, $Q>1.5\times10^4$.

Three extremely large amplitude peaks distinguish themselves in the spectra shown in FIG. 8. These peaks at 580.3 (A), 612.6 (B), and 633.4 (C) nm are coincident with spectral features of the luminescence or inelastic light scattering from silver colloid solutions in a microcavity without R6G. The peaks were assigned to the fundamental or combination Raman modes of sodium citrate. The largest peak B at 612.6 nm is the combination Raman mode (1210+850) $cm^{-1}$ of sodium citrate, the peak A at 580.3 nm corresponds to the 1167 $cm^{-1}$ fundamental Raman mode (this mode is usually very weak), and it is proposed that peak C at 633.4 nm is the combination Raman mode (1410+1210) $cm^{-1}$ or (2×850+956) $cm^{-1}$. Interestingly, not all Raman mode of sodium citrate exhibit intense emission. Rather, the presence of MDR modes selects the emission wavelengths to be amplified depending on the spatial location of the emission sources within the cylindrical microcavity.

As stated previously, the local enhancement in the hot spots of fractals in a microcavity is larger than the average enhancement by as many as six orders of magnitude. Using the factor $10^{14}$ for the fractal hot-spot enhancement and taking into account the multiplicative enhancement factor provided by a microcavity, the local enhancement due to the hot spots in a microcavity can be as large as $10^{18}$.

Hyper-Raman Scattering of Sodium Citrate Molecules Attached to Colloid Particles and Their Fractal Aggregates Hyper-Raman scattering (HRS) is a nonlinear effect, which results in a scattered photon frequency that is characterized as Raman-shifted relative to the higher order harmonics of the excitation frequency. The shift in frequency provides characteristic vibrational information, such as overtones or combination bands, of the scattering molecules, which cannot be obtained by normal Raman scattering or infrared absorption spectroscopy. SEHRS makes it possible to overcome the practical barriers of the intrinsically low intensity of HRS. Furthermore, additional multiplicative enhancement in MDRs of the fractal/microcavity composites provides information on HRS, two-photon and three-photon processes using weak pump lasers like a conventional, CW He-Ne laser.

Extremely broadband spectra of sodium citrate molecules adsorbed on fractals contained within microcavities from about 200 nm to 800 nm using a He-Ne laser, $\lambda_L$=632.8 nm, pump power between 1 and 50 mW were observed. These peaks consist of fundamental, overtone, and combination band Raman spectra of sodium citrate molecules. Normally, i.e., without the use of fractal/microcavities, it would be only possible to detect multi-photon, hyper-Raman scattering with extremely high intensity pulsed laser sources.

Figure 9:
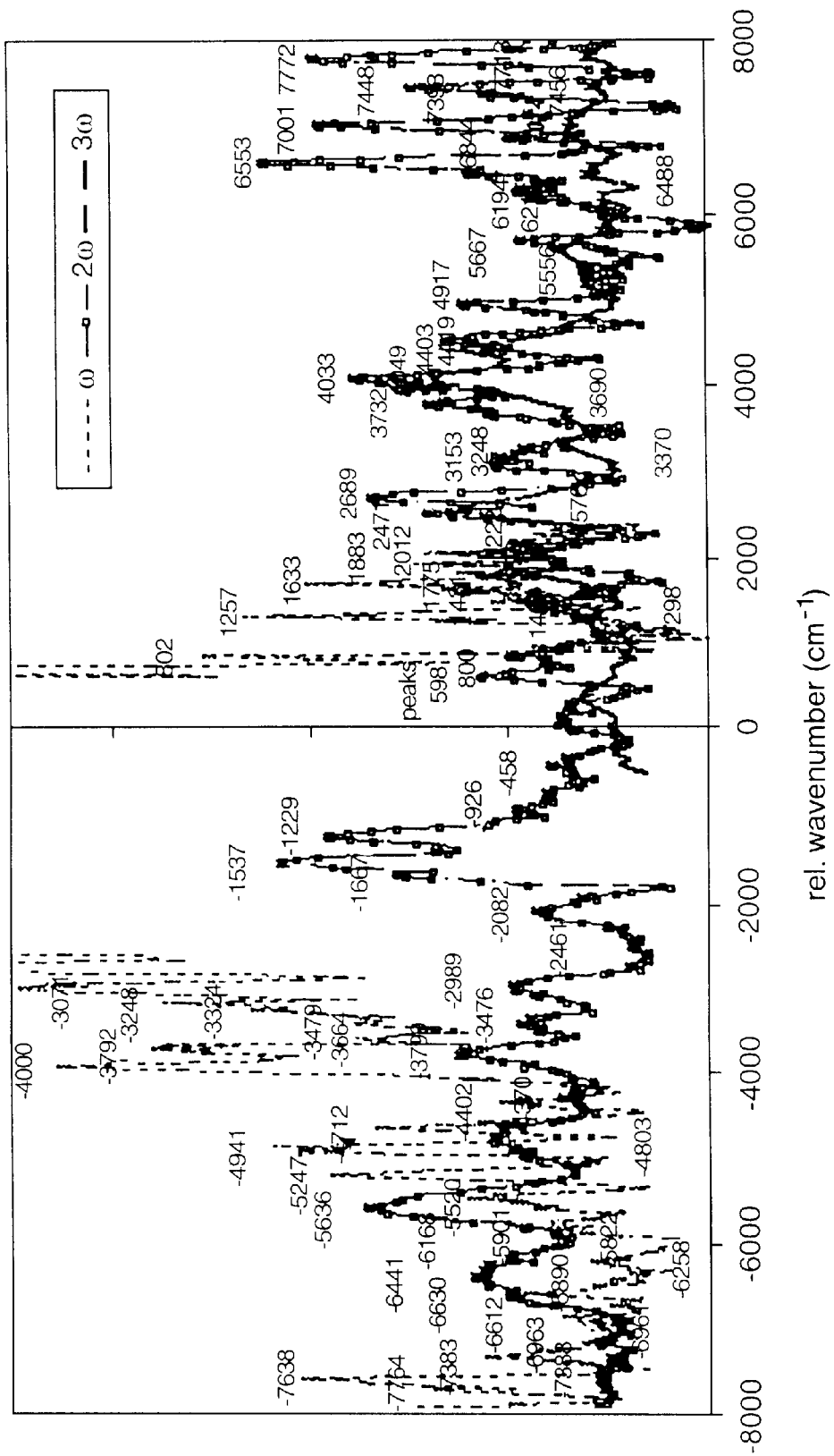
FIG. 9 shows spectra using a conventional Raman-plot for sodium citrate, wherein zero represents the pump frequency; Stokes emissions are plotted on the right and anti-Stokes emissions to the left.

FIG. 9 plots the spectra using a conventional "Raman-plot", where ω denotes the pump frequency, Stokes emissions are plotted to the right, anti-Stokes emissions to the left, and conventional $cm^{-1}$ units are used to denote frequency. The pumps in this plot are: the ω-pump, i.e., the He-Ne laser at 632.8 nm, and the second and third harmonics of the pump laser (the 2ω and 3ω pumps at approximately 316 nm and 211 nm, respectively). FIG. 9 exhibits spectra extending about 8,000 wavenumbers to the Stokes and anti-Stokes sides of the ω, 2ω, and 3ω pump beams. The peaks toward shorter wavelength (2ω and 3ω) regions increase in width since the CCD detector used in this experiment is nearly linear in wavelength, not wavenumber. However, if one accounts for the instrumental error provided by the wavelength separation between adjacent pixels, many sets of Stokes and anti-Stokes Raman bands in the ω, 2ω, and 3ω regions fall within these error margins, i.e., they exhibit the same shifts.

Raman spectra from optically active molecules adsorbed on fractals arise from spatially localized fractal resonance modes, which makes it possible to use less intense pump sources. The enhancement is very large even with fractals not contained within a microcavity. The microcomposites formed by the molecule/fractal/microcavity provides further, multiplicative enhancements of optical responses estimated to be as large as $10^{12}$, for "conventional" Raman and much more for hyper-Raman. For example, the fractal enhancement only for two- and three-photon pumped HRS can be as large as $10^{10}$ and $10^{16}$, respectively. When either the pump or the HRS, or both, waves are coupled to the cavity's MDR, the SEHRS multiplicative enhancement can achieve extremely large values, for example, up to $10^{26}$ for three-photon pumped HRS, provided that both the pump and the HRS waves couple to the MDRs.

Because of this, despite the extremely small hyper-Raman cross-section, the highly nonlinear SEHRS can be obtained in fractal/microcavity composites, even at very low pumps, such as those from He-Ne lasers. The multi-photon hyper-Raman emissions in these systems are fundamental, overtone, and combination scattering of "conventional" Raman bands of the ω, 2ω, or 3ω pump light. The 2ω and 3ω light is generated via the processes of two-photon and three-photon absorption in spatially localized regions of fractals contained in cylindrical microcavities.

Industrial Applicability

The invention is further illustrated by the following non-limiting examples.

EXAMPLE 1

LIDAR

Light detection and ranging (LIDAR) systems are versatile optical instruments that are currently used in a variety of atmospheric applications. LIDARs may be used to obtain: concentrations of a variety of atmospheric constituents such as chemical compounds, dust, volcanic ash, and water vapor; wind velocity and atmospheric turbulence profiles; and ultra-precise geodesy information. All LIDARs operate in a similar manner; a light source, usually a laser, is directed into the atmosphere through transmitter optics such as an optical telescope where it interacts with the atmospheric constituents. Some of the light produced by this interaction is collected by an optical receiver (typically, the transmitter telescope itself) where, for some applications, it is spectrally analyzed, and then input to an optical detector. Optical detectors used in LIDAR systems are typically solid-state photodetectors; although having fairly good optical gain, they are susceptible to noise both from the ambient atmosphere and from the pump laser itself.

The novel characteristics of fractal/microcavity systems discussed above therefore have application to LIDARs. Specifically, light incident on a fractal/microcavity composite is greatly amplified through interactions with either the non-aggregated or aggregated nanoparticles and also with the microcavity resonance modes. In other words, the fractal/microcavity composite of the present invention provides an extremely sensitive optical detector. Raman spectroscopy experiments have repeatedly revealed these sensitive detection properties. In these experiments, extremely weak Raman emission is generated in the fractal/microcavity composite. This emission may be amplified and detected by allowing it to interact with a second optical signal tuned to the same wavelength as the Raman light. Various nonlinear optical interactions may be exploited in this interaction; in these experiments, the process of stimulated resonance Rayleigh scattering was used. However, other nonlinear processes suggest themselves such as four-wave mixing and multi-photon absorption.

In order to realize the process described above with respect to a LIDAR system, the light generated by the atmospheric constituents is input onto a fractal/microcavity composite, irradiated by a suitable pump laser chosen to interact with this light to generate, via a suitable nonlinear process, a light signal to be detected. For the example discussed above, radiation is emitted by an atmospheric constituent, and the pump tuned to this radiation generates enhanced stimulated resonance Rayleigh scattering emission as described above.

Furthermore, a "micro-LIDAR" device has use in a variety of applications. Because of the extremely small size of the fractal/microcavity medium, the micro-LIDAR device can be a hand-held device detecting emissions from a variety of chemical constituents of interest including biological and chemical agents, outgassing from drug and explosive devices, and the presence of poisonous gases such as carbon monoxide.

EXAMPLE 2

OPO

Optical parametric oscillators (OPOs) are useful laser devices that may be tuned in wavelength over a wide range, typically through the visible and near-infrared range. The OPO depends on the nonlinear optical characteristics of materials together with the resonant characteristics of optical cavities. A pump beam is input to a nonlinear optical crystal where it is separated into two beams, a signal beam and an idler beam, wherein the signal is at shorter wavelengths than the pump, and the idler is at longer wavelengths. Under any given operating conditions, the sum of the signal and idler frequencies equals the pump frequency. If the signal or idler beam is input to an optical cavity, the resulting output has all of the characteristics of ordinary laser emission.

To apply the present invention, the nonlinear crystal is replaced by the fractal medium, and the optical cavity is replaced by the microcavity. An incident pump beam excites the signal and idler waves are greatly amplified by the fractal/composite medium. Coupling the signal and idler beams to microcavity resonance modes (MDRs) produces the output laser emission.

Current OPOs are large, expensive, require high-power pump lasers, are very sensitive to thermal and mechanical effects, and are difficult to keep in proper alignment. An OPO based on the fractal/microcavity system is very small (the size of a microcavity), can be pumped with a very low power pump laser, e.g., a HeNe or diode laser, which is very inexpensive being on the order of a few hundred to a few thousand dollars, has excellent thermal and mechanical stability, and will be virtually alignment-free, because MDRs require no alignment. The OPO is of modest power since the pump power will be small, but for many applications, this is not important; for example, laboratory spectroscopy, chemical, biological, and biomedical analysis, some LIDAR applications such as short-range pollution monitoring, and possibly telecommunications.

EXAMPLE 3

Optical Data Storage

Improvement in data storage capacity is of great importance in computer and video disk technology. Given the fact that the optical gain in tractal media is localized in sub-wavelength regions (hot spots) of the fractal, and different wavelengths are amplified in spatially distinct regions of the fractal, the present invention has further application in data storage technology. By irradiation of the fractal with polychromatic, i.e. multi-wavelength light, a distribution of hot spots is generated in the fractal with a different distribution generated for each wavelength. However, if the radiation at a given wavelength has an intensity greater than some threshold value, the so-called photomodification threshold, then the distribution of hot spots in the fractal medium associated with that wavelength becomes "photo-modified." This means that a particular distribution of nanoparticles comprising the fractal medium is physically altered. The consequences of this photomodification for the optical emission is that the absorption of the fractal medium is altered. Moreover, this alteration in absorption is permanent, and a so-called "spectral hole" is burned into the fractal medium at this wavelength. This hole burning effect has use as an optical memory device. The fractal medium "remembers" that a particular wavelength physically altered its fractal structure and not some other wavelength. Because of the sub-wavelength dimension of the hot spots and because of the fact that different wavelengths burn holes in spatially distinct regions of the fractal, the density of information stored in the fractal medium is large, enabling high capacity optical data storage.

EXAMPLE 4

Near-Field Optical Spectroscopy

Near-field optics is an optical measurement method which can achieve spatial resolution much higher than the conventional optical microscopy. The spatial resolution for a conventional optical microscope is limited to approximately one half of the light wavelength, which is several hundred nanometers in the visible spectrum. Near-field optics can achieve 1 nanometer spatial resolution.

There are several successful methods to achieve the superior spatial resolution in near-field optics. M. A. Paesler and P. J. Moyer, *Near-Field Optics: Theory, Instrumentation, and Applications* (Wiley, N.Y., 1996). One method locates the material within a distance shorter than the light wavelength from a tapered end of an optical fiber and detects the light emitted from the material through the optical fiber. Another method uses a tapered end of an optical fiber, located within a distance shorter than the light wavelength from the material, to illuminate the material. Yet another method locates a sharp tip of a vibrating metal wire within a distance shorter than the light wavelength from the material and the light emitted from the material is detected employing a lock-in method. In all of these methodologies, the material to be detected must be located within a distance shorter than the light wavelength from either a tapered end of an optical fiber or a sharp tip of a vibrating metal wire.

Near-field optical spectroscopy is a near-field optical spectroscopic method, which detects chemical compounds and biological materials through their spectroscopic signatures. The material can be any of the following: a single molecule, a plurality of molecules, a nanocrystal, DNA, DNA fragments, amino acids, antigen, antibodies, bacteria, bacterial spores, or viruses. The spectroscopic signatures obtained can be either electronic, vibrational, or rotational spectroscopic signatures, which are often available through published literature. Several types of optical processes can be involved in the near-field optical spectroscopic method including photoluminescence, Raman scattering, hyper-Raman scattering, Broullion scattering, harmonic generation, sum frequency generation, difference frequency generation, and optical Kerr effect.

Figure 10:
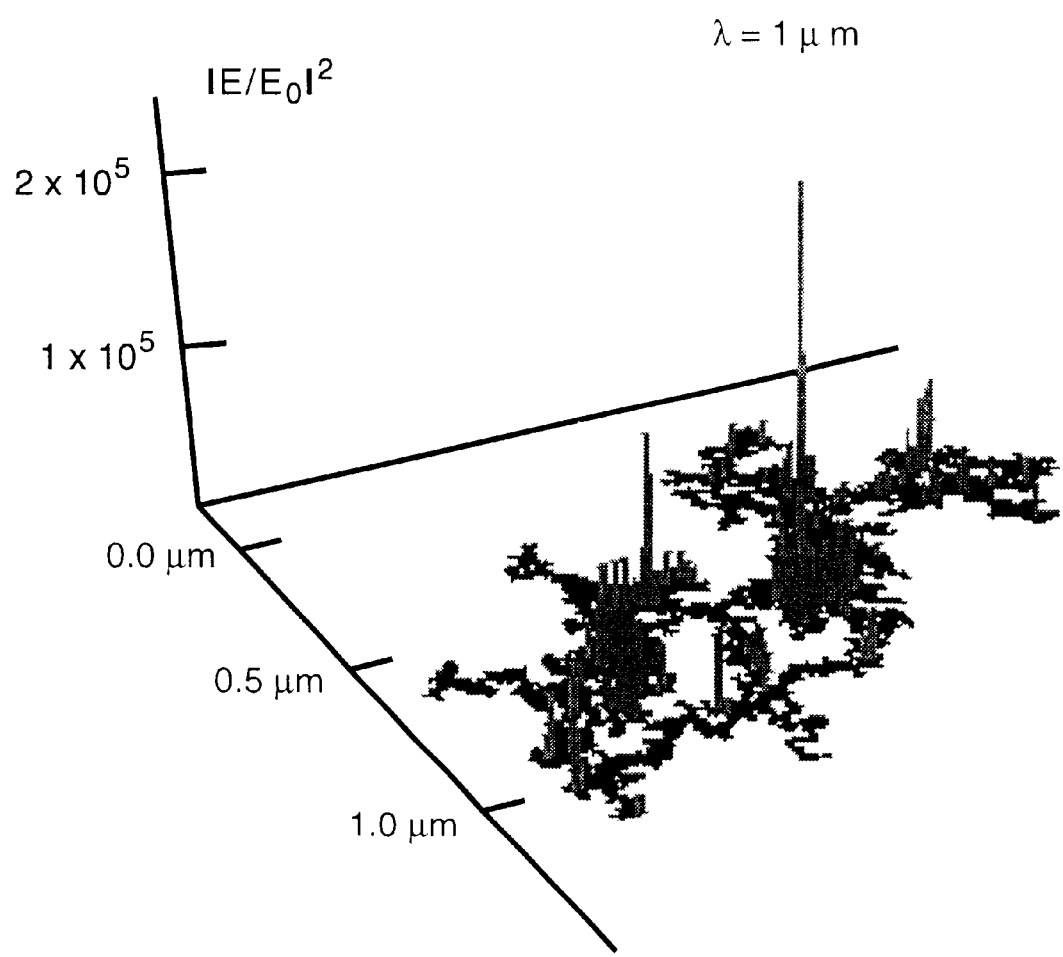
FIG. 10 shows theoretical prediction for enhancement, by factors of up to 100,000, of linear optical intensity for a fractal of silver nanoparticles.
Figure 11A:
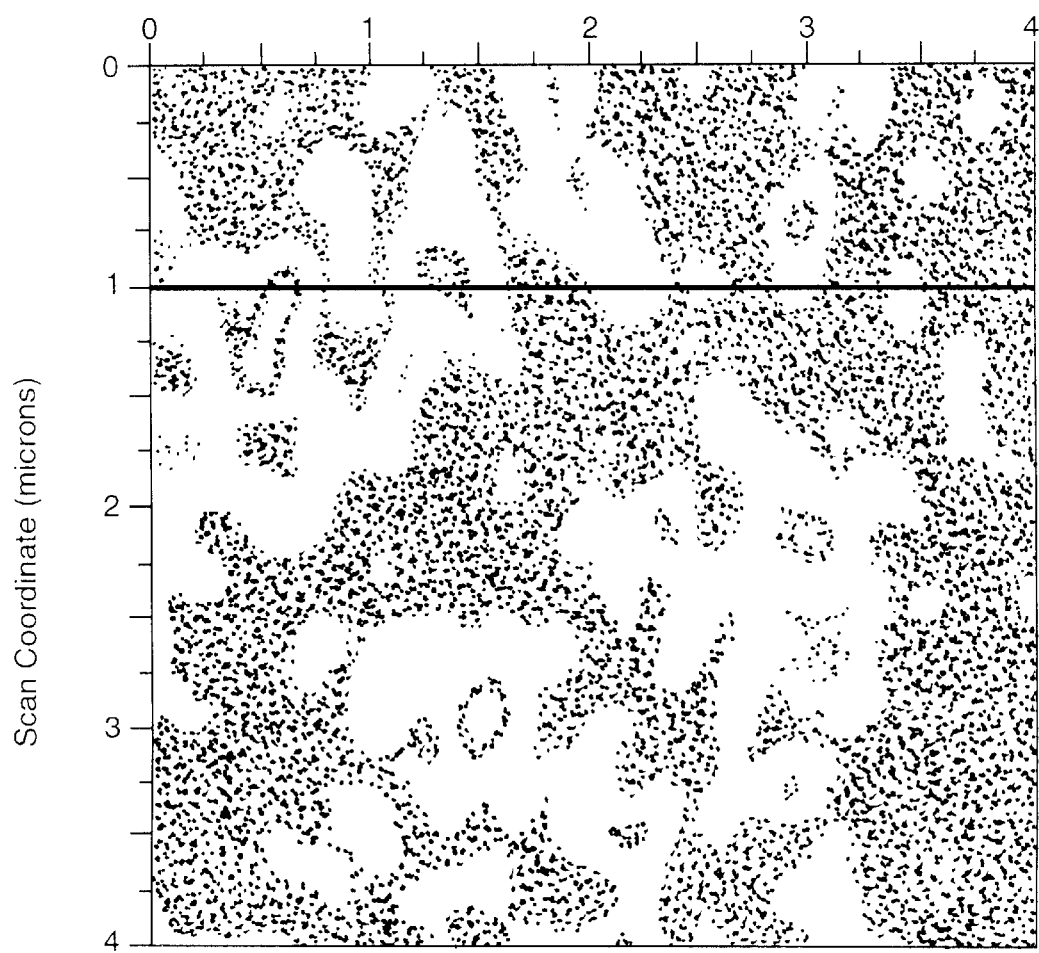
FIGS. 11 a–b show experimental data of linear optical intensity for fractals of silver nanoparticles, collected through an optical fiber, the tapped end of which was located within the light wavelength from the fractals.
Figure 11B:
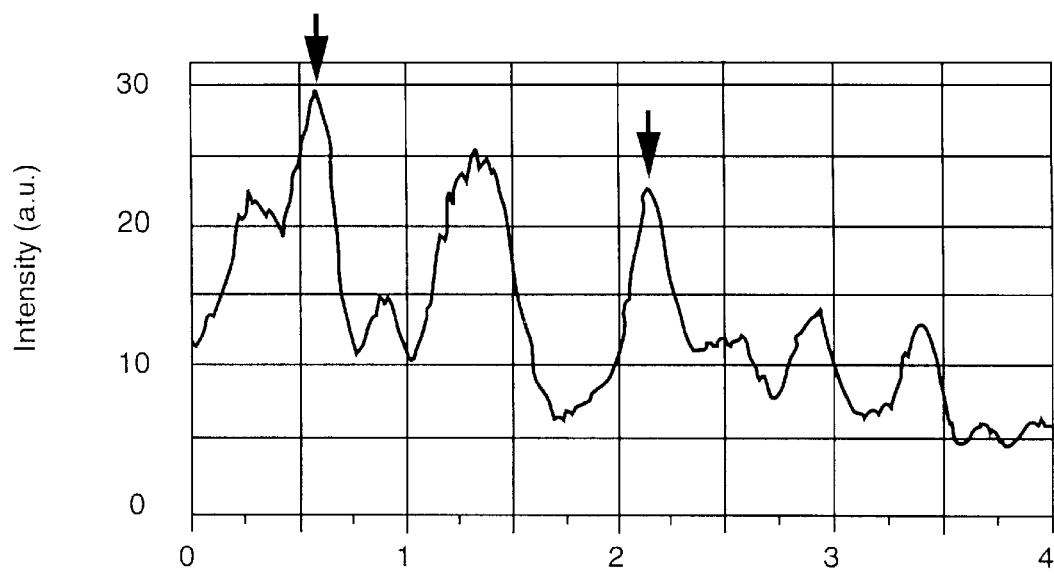

Near-field optical signals can be enhanced by non-aggregated nanoparticles as well as by aggregated nanoparticles (fractals). FIG. 10 shows a theoretical prediction for the enhancement (by factors of up to $10^5$ or 100,000) of linear optical intensity for a fractal of silver nanoparticles. FIG. 11 shows experimental data of linear optical intensity for fractals of silver nanoparticles. The data shown in FIG. 11 were collected through an optical fiber, whose tapped end was located within the light wavelength from the fractals.

Non-aggregated nanoparticles and aggregated nanoparticles, the medium, can enhance near-field optical spectroscopy of a material, when the material is doped onto the medium. In the case where the light signal is detected through the optical fiber, there is an alternative wherein the medium is deposited onto the input end of the optical fiber instead.

Furthermore, a microcavity can enhance near-field optical spectroscopy of a material, where located in the vicinity of the microcavity. A combination of the medium and a microcavity can also enhance near-field optical spectroscopy of a material, where located in the vicinity of the microcavity. The material is doped onto the medium, or, in the case where the light signal is detected through the optical fiber, the medium is deposited onto the input end of the optical fiber.

EXAMPLE 5

Optical Amplifiers

Fractals, microcavities, and fractal/microcavity composites can be utilized for optical amplification. Physical processes that optically amplify include but are not limited to, stimulated emission, optical parametric processes, stimulated Raman processes, stimulated Brilluoin processes, and phase conjugation processes. The utilization of the aforementioned processes for optical amplification are discussed in standard texts.

Optical amplifiers that utilize nonlinear optical processes require an optical pump source and a source of signal photons to be amplified. In conventional nonlinear optical amplifiers one of the following is required for efficient operation: very high pump intensity, very long interaction length, a high quality factor resonator or a combination of those three features.

For example, Yariv in "Quantum Electronics" $3^{rd}$ Ed. pp. 466–467 calculates a stimulated Raman gain coefficient, $g_R=2\times10^{-8} I_\rho cm^{-1}$ where $I_\rho$ represents the pump intensity in watt/$cm^2$, this pump intensity of 1 MW/$cm^2$ to achieve a gain coefficient of a mere 2% per cm. In fiber Raman amplifiers the pump powers are kept at the level of a few watts while the interaction length is spread out over tens of kilometers to achieve an amplifier gain of 1000, (see "Analysis of counter-pumped small-signal fibre Raman amplifiers," by S. R. Chinn, Electronics Letters, Vol. 33, No. 7, pp. 607—608, Mar. 27, 1997). Conventional high quality factor resonators are typically expensive and it is also difficult to couple light into these resonators efficiently.

The fractal, microcavity, and fractal/microcavity systems described herein have the advantages of reducing the required pump power or interaction length by five or more orders of magnitude. For example, a simple 100-micron long single pass fractal/sodium citrate single pass amplifier has generated a gain of 1000 when pumped with a 10 mW source. The Raman small signal gain coefficient for this fractal/sodium citrate amplifier was measured, $g_R$=0.5 $I_\rho cm^{-1}$, and this is clearly over seven orders of magnitude greater than the gain coefficient calculated by Yariv above, thus the low pump power (10 mW) and short interaction length (100 microns) compared to conventional systems. Lastly, the fractal, microcavity, and fractal/microcavity systems eliminate the need for complicated high quality factor cavities.

The advantages described above of the fractal stimulated Raman amplifier are discussed in comparison to the conventional stimulated Raman amplifier. While reference is made explicitly to the stimulated Raman amplifier, comparable results are achieved for the microcavity stimulated Raman amplifier and amplifiers that utilize other nonlinear optical gain processes. Furthermore, larger enhancements are expected when a fractal/microcavity system is utilized for amplification over any of the other amplification processes mentioned above.

EXAMPLE 6

Wavelength Translation Devices

Fractals, microcavities, and fractal/microcavities can be utilized for optical wavelength translation devices. The wavelength translation occurs via one of the following processes: stimulated Raman and stimulated hyper-Raman scattering, Stimulated Broullion scattering, harmonic generation, optical parametric processes, multi-photon emission, four-wave mixing and/or phase conjugation. The utilization of several of the aforementioned processes for optical frequency translation are discussed in standard texts.

Optical wavelength translation devices that utilize non-linear optical processes require one or more optical wavelength beams be sent into the nonlinear device. For example optical harmonic generation only requires that a single beam enter and several harmonic frequencies may exit along with part of the original pump wavelength, while in a four-wave mixing device up to three pump wavelengths may be sent into the nonlinear medium and one signal wavelength exit. In conventional nonlinear optical wavelength translation devices one of the following is required for efficient operation: very high pump intensity, very long interaction length, a high quality factor resonator or a combination of the three features. Just as was the case for the optical amplification one or more of the following advantages will occur, the optical threshold will be reduced by five or more orders of magnitude, the device size may be decreased by five or more orders of magnitude, and the conversion efficiency will be significantly increased. These results apply for all of the wavelength translation processes. The advantages of the fractal, microcavity, and fractal/microcavity for wavelength translation devices based upon the Raman and hyper-Raman emissions are discussed in detail earlier in the sections entitled "Surface-Enhanced Raman Scattering in Sodium Citrate" and "Hyper-Raman Scattering of Sodium Citrate Molecules Attached to Colloid Particles and Their Fractal Aggregates".

While particular optical processes are described above, additional optical processes can be provided when exciting the medium of the present invention and include: photoluminescence, Raman scattering, hyper-Raman scattering, Broullion scattering, harmonic generation, sum frequency generation, difference frequency generation, optical parametric processes, multi-photon absorption, optical Kerr effect, four-wave mixing, and phase conjugation.

The preceding examples can be repeated with similar success by substituting the generically or specifically described reactants and/or operating conditions of this invention for those used in the preceding examples.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. A light emitting apparatus comprising:
   at least one light source;
   a medium, said medium comprising a plurality of nanoparticles selected from the group consisting of non-aggregated nanoparticles, and aggregated nanoparticles comprising fractals; and
   a microcavity, wherein said medium is located in the vicinity of said microcavity to enhance the optical emission.

2. The light emitting apparatus of claim 1 wherein said microcavity comprises a microcavity selected from the group consisting of hollow microcavities and solid microcavities.

3. The light emitting apparatus of claim 2 wherein said microcavity comprises a solid microcavity, and said medium is located on a surface of said solid microcavity.

4. The light emitting apparatus of claim 2 wherein said microcavity comprises a solid microcavity, and said medium is embedded within said solid microcavity.

5. The light emitting apparatus of claim 2 wherein said microcavity comprises a hollow microcavity and said medium is located within said hollow microcavity.

6. The light emitting apparatus of claim 2 wherein said microcavity comprises a hollow microcavity and said medium is located on a surface of said hollow microcavity.

7. The light emitting apparatus of claim 1 wherein said medium is contained within a substance selected from the group consisting of liquid suspensions, gel matrices, and solid matrices.

8. The light emitting apparatus of claim 1 wherein said medium comprises at least one material selected from the group consisting of metals, semi-metals, and semiconductors.

9. The light emitting apparatus of claim 8 wherein said metals comprise at least one metal selected from the group consisting of silver, gold, platinum, copper, aluminum, and magnesium.

10. The light emitting apparatus of claim 8 wherein said semi-metal comprises graphite.

11. The light emitting apparatus of claim 8 wherein said semiconductors comprise at least one semiconductor selected from the group consisting of Group IV, Group III-V, and Group II-VI semiconductors.

12. The light emitting apparatus of claim 1 wherein said medium comprises individual nanoparticles each of an average diameter that is less than the optical wavelength of interest.

13. The light emitting apparatus of claim 1 wherein said microcavity comprises a microcavity selected from the group consisting of cylindrical microcavities, spherical microcavities, spheroidal microcavities, polyhedral microcavities, and optical wave guide microcavities.

14. The light emitting apparatus of claim 1 wherein said microcavity comprises an exterior dimension that is at least twice that of the optical wavelength of interest.

15. The light emitting apparatus of claim 1 wherein said light source emits light of wavelengths between approximately 200 and 100,000 nanometers.

16. The light emitting apparatus of claim 15 wherein said light source emits light of wavelengths between approximately 300 and 2,000 nanometers.

17. The light emitting apparatus of claim 1 wherein said light source emits light comprising between approximately 1 nanowatt and 100 watts of power.

18. The light emitting apparatus of claim 1 further comprising at least one molecule selected from the group consisting of optically active organic and inorganic molecules, adsorbed on a surface of said nanoparticles.

19. The light emitting apparatus of claim 18 wherein said at least one molecule comprises at least one molecule selected from the group consisting of laser dye and sodium citrate molecules.

20. The light emitting apparatus of claim 19 wherein said laser dye comprises a dye selected from the group consisting of xanthene, coumarin, pyrromethene, styryl, cyanine, carbon-bridged, naphthofluorescein-type, acridone, quinalone derivative, p-terphenyl, p-quaterphenyl, and 9-aminoacridine hydrochloride dyes.

21. The light emitting apparatus of claim 1 further comprising at least one molecule selected from the group consisting of optically active organic and inorganic molecules, located within the light wavelength of the surface of said nanoparticles.

22. The light emitting apparatus of claim 21 wherein said at least one molecule comprises at least one molecule selected from the group consisting of laser dye and sodium citrate molecules.

23. The light emitting apparatus of claim 22 wherein said laser dye comprises a dye selected from the group consisting of xanthene, coumarin, pyrromethene, styryl, cyanine, carbon-bridged, naphthofluorescein-type, acridone, quinalone derivative, p-terphenyl, p-quaterphenyl, and 9-aminoacridine hydrochloride dyes.

24. The light emitting apparatus of claim 1 wherein said aggregated nanoparticles comprising fractals comprises at least 10 nanoparticles aggregated to comprise each fractal.

25. The light emitting apparatus of claim 1 wherein said fractals comprise a fractal dimension less than that of the embedding space.

26. A method of enhancing the optical emission of a material comprising the steps of:
 a) doping a medium, the medium comprising a plurality of nanoparticles selected from the group consisting of non-aggregated nanoparticles, and aggregated nanoparticles comprising fractals, with the material;
 b) exciting the doped medium with at least one light source; and
 c) locating the doped medium in the vicinity of a microcavity.

27. The method of claim 26 wherein doping a medium with the material comprises doping with at least one material selected from the group consisting of a single molecule, a plurality of molecules, a nanocrystal, a solid matrix, DNA, DNA fragments, amino acids, antigen, antibodies, bacteria, bacterial spores, and viruses.

28. The method of claim 26 wherein the locating step comprises locating the medium on a surface of a solid microcavity.

29. The method of claim 26 wherein the locating step comprises embedding the medium within a solid microcavity.

30. The method of claim 26 wherein the locating step comprises locating the medium within a hollow microcavity.

31. The method of claim 26 wherein the locating step comprises locating the medium on a surface of a hollow microcavity.

32. The method of claim 26 wherein the step of exciting comprises exciting the doped medium to result in at least one type of optical process selected from the group consisting of photoluminescence, Raman scattering, hyper-Raman scattering, Broullion scattering, harmonic generation, sum frequency generation, difference frequency generation, optical parametric processes, multi-photon absorption, optical Kerr effect, four-wave mixing, and phase conjugation.

33. The method of claim 26 wherein the medium is contained within a substance selected from the group consisting of liquid suspensions, gel matrices, and solid matrices.

34. The method of claim 26 wherein the medium comprises at least one material selected from the group consisting of metals, semi-metals, and semiconductors.

35. The method of claim 34 wherein the metals comprise at least one metal selected from the group consisting of silver, gold, platinum, copper, aluminum, and magnesium.

36. The method of claim 34 wherein the semi-metal comprises graphite.

37. The method of claim 34 wherein the semiconductors comprise at least one semiconductor selected from the group consisting of Group IV, Group III-V, and Group II-VI semiconductors.

38. The method of claim 26 wherein the exciting step comprises emitting light of wavelengths between approximately 200 and 100,000 nanometers.

39. The method of claim 38 wherein the step of emitting light comprises emitting light of wavelengths between approximately 300 and 2,000 nanometers.

40. The method of claim 26 wherein the exciting step comprises emitting light of between approximately 1 nanowatt and 100 watts of power.

41. The method of claim 26 wherein the step of doping further comprises doping with at least one molecule selected from the group consisting of optically active organic and inorganic molecules located within the light wavelength of the surface of the medium.

42. The method of claim 41 wherein the at least one molecule comprises at least one molecule selected from the group consisting of laser dye and sodium citrate molecules.

43. The method of claim 42 wherein the laser dye comprises a dye selected from the group consisting of xanthene, coumarin, pyrromethene, styryl, cyanine, carbon-bridged, naphthofluorescein-type, acridone, quinalone derivative, p-terphenyl, p-quaterphenyl, and 9-aminoacridine hydrochloride dyes.

44. An amplifying apparatus having a gain greater than 1.2, said apparatus comprising:
 at least one light source;
 a microcavity; and
 a medium, said medium comprising a plurality of nanoparticles selected from the group consisting of non-aggregated nanoparticles, and aggregated nanoparticles comprising fractals, said medium located in the vicinity of said microcavity to enhance optical emission.

45. A method of amplification comprising the steps of:
 a) providing a medium comprising a plurality of nanoparticles selected from the group consisting of non-aggregated nanoparticles, and aggregated nanoparticles comprising fractals;
 b) locating the medium in the vicinity of a microcavity to amplify optical emission; and
 c) exciting the medium with at least one light source.

46. The method of claim 45 wherein locating the medium in the vicinity of a microcavity to amplify optical emission further comprises amplifying optical emissions via at least one process selected from the group of processes consisting of stimulated emission of photons, stimulated Raman scattering, stimulated hyper-Raman scattering, stimulated Broullion scattering, optical parametric amplification, multi-photon emission, four-wave mixing, and phase conjugation.

* * * * *